US010130598B2

(12) United States Patent
Geschwind et al.

(10) Patent No.: US 10,130,598 B2
(45) Date of Patent: Nov. 20, 2018

(54) METHODS AND COMPOSITIONS FOR ADMINISTRATION OF 3-HALOPYRUVATE AND RELATED COMPOUNDS FOR THE TREATMENT OF CANCER

(71) Applicant: The Johns Hopkins University, Baltimore, MD (US)

(72) Inventors: Jean-Francois Geschwind, Potoman, MD (US); Mustafa Vali, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/284,014

(22) Filed: Oct. 3, 2016

(65) Prior Publication Data

US 2017/0224641 A1 Aug. 10, 2017

Related U.S. Application Data

(62) Division of application No. 12/583,598, filed on Aug. 21, 2009, now Pat. No. 9,492,417.

(60) Provisional application No. 61/097,408, filed on Sep. 16, 2008, provisional application No. 61/090,793, filed on Aug. 21, 2008.

(51) Int. Cl.
*A61K 31/22* (2006.01)
*A61K 31/194* (2006.01)
*A61K 31/19* (2006.01)
*A61K 45/06* (2006.01)
*A61K 47/02* (2006.01)

(52) U.S. Cl.
CPC .............. *A61K 31/19* (2013.01); *A61K 45/06* (2013.01); *A61K 47/02* (2013.01)

(58) Field of Classification Search
CPC ............................. A61K 31/22; A61K 31/194
See application file for complete search history.

(56) References Cited

U.S. PATENT DOCUMENTS

| | | | |
|---|---|---|---|
| 4,235,871 A | 11/1980 | Papahadjopoulos et al. | |
| 4,337,760 A | 7/1982 | Rubin | |
| 4,536,387 A | 8/1985 | Sakamoto et al. | |
| 4,737,323 A | 4/1988 | Martin et al. | |
| 5,213,804 A | 5/1993 | Martin et al. | |
| 5,759,547 A | 6/1998 | Maione | |
| 5,759,837 A | 6/1998 | Kuhajda et al. | |
| 5,854,067 A | 12/1998 | Newgard et al. | |
| 6,284,746 B1 | 9/2001 | Szente et al. | |
| 6,284,786 B1 | 9/2001 | Casciari et al. | |
| 6,312,662 B1 | 11/2001 | Erion et al. | |
| 6,448,030 B1 | 9/2002 | Rust et al. | |
| 6,670,330 B1 | 12/2003 | Lampidis et al. | |
| 7,547,673 B2 | 6/2009 | Ko et al. | |
| 8,119,116 B2 | 2/2012 | Ko et al. | |
| 9,737,487 B2 | 8/2017 | Geschwind et al. | |
| 2001/0046997 A1 | 11/2001 | Abraham et al. | |
| 2002/0006915 A1 | 1/2002 | Mack Strong et al. | |
| 2002/0068711 A1 | 6/2002 | Pedersen et al. | |
| 2003/0018166 A1 | 1/2003 | Sacchettini et al. | |
| 2003/0087961 A1* | 5/2003 | Ko ......................... A61K 31/19 514/557 |
| 2003/0139331 A1 | 7/2003 | Martin et al. | |
| 2004/0029826 A1 | 2/2004 | Sokoloff et al. | |
| 2004/0167079 A1* | 8/2004 | Tidmarsh ............... A61K 31/70 514/23 |
| 2004/0167196 A1 | 8/2004 | Tidmarsh | |
| 2006/0058383 A1 | 3/2006 | Huang et al. | |
| 2006/0154867 A1 | 7/2006 | Sokoloff et al. | |
| 2010/0330197 A1 | 12/2010 | Higashiguchi et al. | |
| 2012/0128757 A1 | 5/2012 | Kikuchi et al. | |
| 2014/0220112 A1 | 8/2014 | Szoka, Jr. et al. | |

FOREIGN PATENT DOCUMENTS

| | | |
|---|---|---|
| DE | 19814815 A1 | 10/1999 |
| WO | WO-1994/16733 A1 | 8/1994 |
| WO | WO-1994/23697 A1 | 10/1994 |
| WO | WO-1996/14057 A1 | 5/1996 |
| WO | WO-1997/04104 A2 | 2/1997 |
| WO | WO-2004/002455 A1 | 1/2004 |
| WO | WO-2004/076454 A1 | 9/2004 |
| WO | WO-2005/107712 A1 | 11/2005 |
| WO | WO-2006/010073 | 1/2006 |
| WO | WO-2007/097989 | 8/2007 |
| WO | WO-2010/021750 A2 | 2/2010 |
| WO | WO-2012/118376 A1 | 9/2012 |
| WO | WO-2014/004651 A1 | 1/2014 |

OTHER PUBLICATIONS

U.S. Appl. No. 61/090,793, Geschwind.
U.S. Appl. No. 61/097,408, Geschwind.
U.S. Appl. No. 61/165,239, Geschwind.
Abraham et al., "An evaluation of transmembrane ion gradient-mediated encapsulation of topotecan within liposomes," J Control Release, 96:449-461 (2004).
Ackermann et al., "Polo-like kinase 1 is a therapeutic target in high-risk neuroblastoma," Clinical Cancer Res, 17:731-741 (2011).
Albers et al., "Cyclodextrin derivatives in pharmaceutics," Crit Rev Ther Drug, 12:311-337 (1995).
Ando, et al., "Hepatic Arterial Infusion Chemotherapy for Advanced Hepatocellular Carcinoma with Portal Vein Tumor Thrombosis," Cancer, 95: 588-595 (2002).
Arafat et al., "Toxicities Related to intraarterial Infusion of Cisplatin and Etoposide in Patients with Brain Tumors," J. of Neuro-oncology, 42:73-77 (1999).
Archived webpage from Touch Oncology; https://web.archive.org/web/20070211104624/https://www.touchoncologicaldisease.com/articles.cfm?article_id=6103&level=2.

(Continued)

*Primary Examiner* — Samira J Jean-Louis
(74) *Attorney, Agent, or Firm* — Foley Hoag LLP; Hathaway P. Russell; Thi K. Dio

(57) ABSTRACT

The present disclosure relates to the discovery that compounds of the invention, particularly 3-bromopyruvate and related compounds, can be safely administered at concentrations effective for the treatment of cancer when formulated with an acidity of greater than or equal to pH of 2 and less than or equal to a pH of 6. Disclosed herein are novel and improved methods and compositions for the treatment of cancer using 3-halopyruvate and related compounds.

9 Claims, 15 Drawing Sheets

(56) References Cited

OTHER PUBLICATIONS

Ascenso et al., "Novel tretinoin formulations: a drug-in-cyclodextrin-in-liposome approach," Informa HealthCare, 23(3):211-219 (2013).
Badr-Eldin et al., "Inclusion complexes of tadalafil with natural and chemically modified beta-cyclodextrins. I: preparation and in-vitro evaluation," Eur J Pharm Biopharm, 70:819-827 (2008).
Bar et al., "Sorbitol Removal by the Metastatic Liver: A Predictor of Systemic Toxicity of Intra-arterial Chemotherapy in Patients with Liver Metastases," J. of Hepatology, 30:1112-1118 (1999).
Barenholz, "Relevancy of drug loading to liposomal formulation therapeutic efficacy," J Lipos Res, 13:1-8 (2003).
Baryshnikov, [Nanostructured liposomal systems as transport agents for anticancer drugs]. Vestnik Rossiiskoi akademii meditsinskikh nauk/Rossiiskaia akademiia meditsinskikh nauk, 23-31 (2012).
Brown et al., "Pharmacodynamic and toxicokinetic evaluation of the novel MEK inhibitor, PD0325901, in the rat following oral and intravenous administration," Cancer Chemoth Pharm, 59:671-679 (2007).
Calleja et al., "Molecular buckets: cyclodextrins for oral cancer therapy," Therapeutic Delivery, 3: pp. 1-32 (2012).
Cao et al., "The physicochemical characteristics of freeze-dried scutellarin-cyclodextrin tetracomponent complexes," Drug Dev Ind Pharm, 31:747-756 (2005).
Challa et al., "Cyclodextrins in Drug Delivery: An Updated Review," AAPS PharmSciTech 2005, 6(2): Article 43 E329-E357 (2005).
Chandran et al., "Recent trends in drug delivery systems: liposomal drug delivery system—preparation and characterisation," Indian J Exper Biol, 35:801-809 (1997).
Chang et al., "Local Toxicity of Hepatic Arterial Infusion of Hexokinase II Inhibitor, 3-Bromopyruvate: In Vivo Investigation in Normal Rabbit Model". Academic Radiology, 14(1):85-92 (2007).
Chapiro et al., "Systemic delivery of microencapsulated 3-bromopyruvate for the therapy of pancreatic cancer," Clin Cancer Res, 20(24):6406-6417 (2014).
Chen et al., "The Warburg effect and its cancer therapeutic implications," J Bioenerg Biomembr, 39: 267-274 (2007).
Chertok et al., "Drug delivery interfaces in the 21st century: from science fiction ideas to viable technologies," Mol Pharmaceutics, 10:3531-3543 (2013).
Choi et al., "Mechanism of active targeting in solid tumors with transferrin-containing gold nanoparticles," Proc Natl Acad Sci U S A, 107:1235-1240 (2010).
Cohen and Kemeny, "An Update on Hepatic Arterial Infusion Chemotherapy for Colorectal Cancer," The Oncologist, 8: 553-556 (2003).
Costello et al., "Evidence for Changed in RREB-1, ZIP3, and Zinc in the Early Development of Pancreatic Adenocarcinoma," J Gastrointest Canc, 43: 570-578 (2012).
Cover e-mail from Dr. X to Dr. Y enclosing attachments and attachments (Feb. 10, 2009).
Cucinotta et al., "The 6-derivative of -cyclodextrin with succinic acid: a new chiral selector for CD-EKC," J Pharmaceut Biomed Analysis, 37:1009-1014 (2005).
Cui et al., "Development of pegylated liposomal vincristine using novel sulfobutyl ether cyclodextrin gradient: Is improved drug retention sufficient to surpass DSPE—PEG-induced drug leakage?," J Pharm Sci, 100:2835-2848 (2011).
Curriculum vitae of Professor Margarida Casal, 1 page.
Davis et al., "Evidence of RNAi in humans from systemically administered siRNA via targeted nanoparticles," Nature, 464:1067-1070 (2010).
Declaration dated Dec. 14, 2015 by Professor Stanislaw Ulaszewski, University of Wroclaw, Poland.
Declaration dated Sep. 15, 2016 by Dr. Harrie Verhoeven.
Declaration dated Sep. 15, 2016 by Dr. Young Ko.
Declaration dated Dec. 17, 2015 by Professor Margarida Casal, University of Minho, Portugal.
Deposition of Dr. Geschwind on Mar. 21, 2006, in *Ko v. The Johns Hopkins University, et al.*, 05-CV-1475-WDQ (2005), in the US District Court for the District of Maryland (selected pages).
Dhule et al., "Curcumin-loaded ?-cyclodextrin liposomal nanoparticles as delivery vehicles for osteosarcoma," Nanomedicine: Nanotechnology, Biology and Medicine, 8:440-451 (2012).
DiFeo, "Drug Product Development: A Technical Review of Chemistry, Manufacturing, and Controls Information for the Support of Pharmaceutical and Compound Licensing Activities", Drug Dev Industrial Pharm 29(9):939-958 (2003).
Ding et al., "Combined gene expression profiling and RNAi screening in clear cell renal cell carcinoma identify PLK1 and other therapeutic kinase targets," Cancer Res, 71:5225-5234 (2011).
Ellis et al., "A phase I open-label dose-escalation study of intravenous BI 2536 together with pemetrexed in previously treated patients with non-small-cell lung cancer," Clin Lung Cancer, 14:19-27 (2013).
Email #1 entitled "BrPyruvate HCC" from Dr. X to Dr. Y (names redacted) (Oct. 7, 2008).
Email #2, reply from Dr. Young Ko to Dr. Harrie Verhoeven on Oct. 7, 2008. Unredacted Copy.
Email #2: Reply to Email #1 from Dr. Y to Dr. X (Oct. 7, 2008).
Email #3, reply from Dr. Harrie Herhoeven to Dr. Young Ko on Oct. 7, 2008. Unredacted Copy.
Email from the American Board of Radiology (ABR) to the Opponent, dated Mar. 25, 2015.
Ethical Approval Letter from Prof. Dr. Med. Sebastian Harder to Prof. Dr. Thomas Vogl (Feb. 23, 2009).
Extended European Search Report issued by the European Patent Office in corresponding Application No. 15737117.0, dated Jun. 2, 2017.
Extended European Search Report issued by the European Patent Office in corresponding Application No. EP 15737304.4, dated Oct. 23, 2017.
Fahr et al., "Drug delivery strategies for poorly water-soluble drugs," Expert Opin Drug Del, 4:403-416 (2007).
Fang et al., "The EPR effect: unique features of tumor blood vessels for drug delivery, factors involved, and limitations and augmentation of the effect," Adv Drug Deliv Rev, 63:136-151 (2011).
Fenske et al., "Liposomal nanomedicines," Expert Opin Drug Del, 5:25-44 (2008).
Fiebig et al., "Relevance of Tumor Models for Anticancer Drug Development," Contrib. Oncol. Basel. Karger, 54:109-120 (1999).
Fremin et al., "From basic research to clinical development of MEK1/2 inhibitors for cancer therapy," J Hematol Oncol, 3:8 (2010).
Frost et al., "Phase i study of the Plk1 inhibitor BI 2536 administered intravenously on three consecutive days in advanced solid tumours," Current Oncol, 19:e28-35 (2012).
Geschwind et al., "Novel Therapy for Liver Cancer: Direct Intraarterial Injection of a Potent Inhibitor of ATP Production," Cancer Research, 62:3909-3913 (2002).
Geschwind, et al., "Effects of intraarterial delivery of 3-bromopyruvate on tumor apoptosis: Comparison between 1 hr. infusion and serial bolus injections in an animal model of liver cancer," American Society of Clinical Oncology, Gastrointestinal Cancers Symposium, Abstract No. 216 (2006).
Geschwind, et al., "Recently elucidated energy catabolism pathways provide opportunities for novel treatments in hepatocellular carcinoma," Expert Rev Anticancer Ther, 4(3): 449-457 (2004).
Glick et al., "The antitumor agent 3-bromopyruvate has a short half-life at physiological conditions," Biochem Bioph Res Co. 452(1): 170-173 (2014).
Gobin et al., "Intraarterial Chemotherapy for Brain Tumors by Using a Spatial Dose Fractionation Algorithm and Pulsatile Delivery," Radiology, 218(3):724-732 (2001).
Godin et al., "Repeat Dose Toxicity Studies of 3-Bromopyruvate in Rats Following Oral and Intraperitoneal Administration". American College of Toxicology, 34th Annual Meeting Program, San Antonio, Texas, Abstract P304, Nov. 3-6, 2013.
Grinshtein et al., "Small molecule kinase inhibitor screen identifies polo-like kinase 1 as a target for neuroblastoma tumor-initiating cells," Cancer Res, 71:1385-1395 (2011).

(56) References Cited

OTHER PUBLICATIONS

Grosse et al., "In Vitro Modulation of Doxorubicin and Docetaxel Antitumoral Activity by Methyl-Beta-cyclodextrin," Eur J Cancer, 34(1): 168-174 (1998).
Gubernator, "Active methods of drug loading into liposomes: recent strategies for stable drug entrapment and increased in vivo activity," Expert Opin Drug Del, 8:565-580 (2011).
Hamada et al., "Enhancement of Water-Solubility and Bioactivity of Paclitaxel Using Modified Cyclodextrins," J Biosci Bioeng, 102(4): 369-371 (2006).
Haran et al., "Transmembrane ammonium sulfate gradients in liposomes produce efficient and stable entrapment of amphipathic weak bases," Biochimica Biophys Acta, 1151:201-215 (1993).
Haura et al., "A phase II study of PD-0325901, an oral MEK inhibitor, in previously treated patients with advanced non-small cell lung cancer," Clin Cancer Res, 16:2450-2457 (2010).
Heidel et al., "Clinical developments in nanotechnology for cancer therapy," Pharmaceut Res, 28:187-199 (2011).
Higashi, T. et al., "Relationship Between Retention Index in Dual-Phase 18F-FDG PET, and Hexokinase-II and Glucose Transporter-1 Expression in Pancreatic Cancer," J Nucl Med, 43:173-180 (2002).
Hofheinz et al., "An open-label, phase I study of the polo-like kinase-1 inhibitor, BI 2536, in patients with advanced solid tumors," Clin Cancer Res, 16:4666-4674 (2010).
Huang et al., "PD0325901, a mitogen-activated protein kinase kinase inhibitor, produces ocular toxicity in a rabbit animal model of retinal vein occlusion," J Ocul Pharmacol Ther, 25:519-530 (2009).
Hubbell et al., "Translating materials design to the clinic," Nature Mater, 12:963-969 (2013).
Huwyler et al., "Tumor targeting using liposomal antineoplastic drugs," Int J Nanomedicine, 3:21-29 (2008).
International Search Report and Written Opinion for International Application No. PCT/US2015/011342 dated Jul. 2, 2015.
International Search Report dated Jul. 2, 2015 from PCT/US2015/011344.
International Search Report dated Jun. 3, 2008 from PCT/US2007/087740.
International Search Report dated May 3, 2010 from PCT/US2009/004789.
Irie et al., "Pharmaceutical applications of cyclodextrins. III. Toxicological issues and safety evaluation," J Pharmaceut Sci, 86:147-162 (1997).
Johns Hopkins Medical Institutions Office of Communications and Public Affairs "Energy Blocker May Be Potential Liver Cancer Treatment," www.hopkinsmedicine.org/press/2002/July020715.htm.
Kanasty et al., "Delivery materials for siRNA therapeutics," Nat Mater, 12:967-977 (2013).
Kerr et al., "Phase I Clinical and Pharmacokinetic Study of Leucovorin and Infusional Hepatic Arterial Flurouracil," J. of Clinical Oncology, 13(12):2968-2972 (1995).
Kim et al., "Apoptosis-inducing Antitumor Efficacy of Hexokinase II inhibitor in Hepatocellular Carcinoma", Mol Cancer Ther, 6(9):2554-62 (2007).
Kita et al., "Drug delivery vehicles with improved encapsulation efficiency: taking advantage of specific drug-carrier interactions," Expert Opin Drug Del, 8:329-342 (2011).
Ko et al., "Advanced Cancers: Eradication in All Cases Using 3-bromopyruvate Therapy to Deplete ATP," BBRC, 324(1):269-275 (2004).
Ko et al., "Advanced Cancers: Eradication in All Cases Using 3-bromopyruvate Therapy to Deplete ATP," Press Release, Nov. 5, 2004.
Ko et al., "Glucose catabolism in the Rabbit VX2 Tumor Model for Liver Cancer: Characterization and Targeting Hexokinase," Cancer Letters, 173:83-91 (2001).
Ko et al., "Metabolic Properties of the Rabbit VX2 Tumor Model Following Liver Implantation: Role for Hexokinase," Cancer Research, 42:519 (2001).
Ko, et al., "A translational study "case report" on the small molecule "energy blocker" 3-bromopyruvate (3BP) as a potent anticancer agent: from bench side to bedside," J Bioenerg Biomembr, 44: 163-170 (2012).
Kostron et al., "Photodynamic Treatment of Malignant Brain Tumors," Jg 102, Heft 18:531-535 (1990).
Lapenda et al., "Encapsulation of trans-dehydrocrotonin in liposomes: an enhancement of the antitumor activity," J Biomed Nanotechnol, 9:499-510 (2013).
Laza-Knoerr et al., "Cyclodextrins for drug delivery," J Drug Target, 18:645-656 (2010).
Lenart et al., "The small-molecule inhibitor BI 2536 reveals novel insights into mitotic roles of polo-like kinase 1," Curr Biol, 17:304-315 (2007).
Letter from Professor Stanislaw Ulazewski, Institute of Genetics and Microbiology, University of Wraclaw, Poland. (Dec. 18, 2014).
Liapi and Geschwind, "Transcatheter Arterial Chemoembolisation (TACE) for HCC—Classic Concepts and Future Evolution," European Oncological Disease, 1(1): 47-52 (2006).
Lim et al., "Polymer-associated liposomes as a novel delivery system for cyclodextrin-bound drugs," J Colloid Interf Sci, 320(2):460-468 (2008).
Lin et al., "Effects of 90Y-Microspheres on Liver Tumors: Comparison of Intratumoral Injection Method and Intra-Arterial Injection Method," The J. of Nuclear Medicine, 41(11):1892 (2000).
Liu et al., "Inhibition of polo-like kinase 1 leads to the suppression; of osteosarcoma cell growth in vitro and in vivo," Anticancer Drugs, 22:444-453 (2011).
LookChem, "Bromopyruvic acid," http://www.lookchem.com/Bromopyruvic-acid/, retrieved online on Feb. 2, 2016.
LoRusso et al., "Phase I pharmacokinetic and pharmacodynamic study of the oral MAPK/ERK kinase inhibitor PD-0325901 in patients with advanced cancers," Clin Cancer Res, 16:1924-1937 (2010).
MacDiarmid et al., "Bacterially derived 400 nm particles for encapsulation and cancer cell targeting of chemotherapeutics," Cancer Cell, 11:431-445 (2007).
Madden et al., "The accumulation of drugs within large unilamellar vesicles exhibiting a proton gradient: a survey," Chem Phys Lipids, 53:37-46 (1990).
Maeda et al., "The EPR effect for macromolecular drug delivery to solid tumors: Improvement of tumor uptake, lowering of systemic toxicity, and distinct tumor imaging in vivo," Adv Drug Deliv Rev, 65:71-79 (2013).
Malaekeh-Nikouei et al., "Double loading of cyclosporine A in liposomes using cyclodextrin complexes," PDA J Pharm Sci Technol, 63:139148 (2009).
Mamot et al., "Extensive distribution of liposomes in rodent brains and brain tumors following convection-enhanced delivery," J Neurooncol, 68:1-9 (2004).
Maruyama, "Intracellular targeting delivery of liposomal drugs to solid tumors based on EPR effects," Adv Drug Deliver Rev, 63:161-169 (2011).
Maryland Board of Physicians Practitioner Profile of Dr Geshwind, dated Aug. 5, 2015.
Mastumura et al., "A new concept for macromolecular therapeutics in cancer chemotherapy: mechanism of tumoritropic accumulation of proteins and the antitumor agent smancs," Cancer Res, 46(12 Pt 1):6387-6392 (1986).
Material Safety Data Sheet for Idarubicin hydrochloride (Bedford Laboratories) (Dec. 10, 2005).
Material Safety Data Sheet for Idarubicin hydrochloride (Teva Sicor) (Aug. 3, 2007).
Mathupala et al., "Glucose Catabolism in Cancer Cells," The J. of Biological Chemistry, 276(46):43407-43412 (2001).
Maurer-Spurej et al., "Factors influencing uptake and retention of amino-containing drugs in large unilamellar vesicles exhibiting transmembrane pH gradients," Biochim Biophys Acta, 1416(1-2):1-10 (1999).
Mendonça et al., "Enhanced antiproliferative activity of the new anticancer candidate LPSF/AC04 in cyclodextrin inclusion complexes encapsulated into liposomes," AAPS PharmSciTech, 13:1355-1366 (2012).

(56) References Cited

OTHER PUBLICATIONS

Meng et al., "Induction of mitotic cell death by overriding G2/M checkpoint in endometrial cancer cells with non-functional p53," Gynecol Oncol, 128:461-469 (2013).
Miccoli, L. et al., "Intracellular pH Governs the Subcellular Distribution of Hexokinase in a Glioma Cell Line," Biochem. J., 313:957-962 (1996).
Minn, H. et al., "Determination of 2-fluoro-2-deoxy-D-Glucose Uptake and ATP Level for Evaluating Drug Effects in Neoplastic Cells," Res Exp Med, 191:27-35 (1991).
Modi et al., "Enhanced active liposomal loading of a poorly soluble ionizable drug using supersaturated drug solutions," J Control Release, 162:330-339 (2012).
Moses et al., "Beta Cyclodextrin-Insulin-Encapsulated Chitosan/Alginate Matrix: Oral Delivery System," J Appl Ploym Sci 75: 1089-1096 (2000).
Mross et al., "A randomised phase II trial of the Polo-like kinase inhibitor BI 2536 in chemo-naïve patients with unresectable exocrine adenocarcinoma of the pancreas—a study within the Central European Society Anticancer Drug Research (CESAR) collaborative network," Br J Cancer, 107:280-286 (2012).
Mross et al., "Phase I dose escalation and pharmacokinetic study of BI 2536, a novel Polo-like kinase 1 inhibitor, in patients with advanced solid tumors," J Clin Oncol, 26:5511-5517 (2008).
Mura et al., "Stimuli-responsive nanocarriers for drug delivery," Nat Mater, 12:991-1003 (2013).
Musacchio et al., "Recent developments in lipid-based pharmaceutical nanocarriers," Front Biosci, 16:1388-1412 (2011).
Nappi et al., "Identification of Polo-like kinase 1 as a potential therapeutic target in anaplastic thyroid carcinoma," Cancer Res, 69:1916-1923 (2009).
National Cancer Institute (NCI) in vivo cancer screen data L1210, Leukemia (intraperitoneal) in B6D2F1 (DBF1) mice.
Nelson, K. et al., "3-Bromopyruvate Kills Cancer Cells in Animals," The Lancet Oncology, 3(9):524 (2002) Abstract Only.
NIH Grant Award No. 1 R01CA100883-A0, submitted 202 (redacted). Project title: "Therapy for Liver Cancer by Targetting Energy Metabolism," Principle Investigator: JF Geschwind.
NIH Grant Award No. 5 R01CA100883-02, Issue Date Mar. 30, 2006. Project title: "Therapy for Liver Cancer by Targeting Energy Metabolism," Principle Investigator: JF Geschwind.
NIH Grant Award R01 CA100803-01A2 to Dr. Geschwind, Mar. 10, 2005 (selected pages).
Notice of Allowance for U.S. Appl. No. 14/643,603 dated Jul. 12, 2017.
Office Action Issued in U.S. Appl. No. 10/243,350 dated Dec. 16, 2004.
Office Action Issued in U.S. Appl. No. 10/243,550 dated Aug. 21, 2007.
Office Action Issued in U.S. Appl. No. 10/243,550 dated Feb. 10, 2006.
Office Action Issued in U.S. Appl. No. 10/243,550 dated Jul. 1, 2005.
Office Action Issued in U.S. Appl. No. 10/243,550 dated Jun. 24, 2008.
Office Action Issued in U.S. Appl. No. 10/243,550 dated Nov. 30, 2006.
Office Action Issued in U.S. Appl. No. 10/243,550 dated Oct. 3, 2008.
Okamatsu et al., "Folate-Appended Beta-Cyclodextrin as a Promising Tumor Targeting Carrier for Antitumor Drugs in Vitro and in Vivo," Bioconjugate Chem, 24: 724-733 (2013).
Pedersen et al., "Mitochondrial Bound Type II Hexokinase: a Key Player in the Growth and Survival of Many Cancers and an Ideal Prospect for Therapeutic Intervention," Biochimica and Biophysics Acta, 1555:14-20 (2002).
Pedersen, P., ""Energy Blocker" Kills Big Tumors in Rats," Audio File—Johns Hopkins Medicine, Office of Corporate Communications, Oct. 14, 2004.
Peer et al., "Nanocarriers as an emerging platform for cancer therapy," Nat Nanotechnol, 2:751-760 (2007).
Rahman et al., "Native and β-cyclodextrin-enclosed curcumin: entrapment within liposomes and their in vitro cytotoxicity in lung and colon cancer," J Drug Deliv, 19:346-353 (2012).
Rajewski et al., "Pharmaceutical applications of cyclodextrins. 2. In vivo drug delivery," J Pharmaceut Sci, 85:1142-1169 (1996).
Rothbarth et al., "Melphalan Antitumor Efficacy and Hepatotoxicity: The Effect of Variable Infusion Duration in the Hepatic Artery," The Journal of Pharmacology and Experimental Therapeutics, 305(3):1098-1103 (2003).
Saito et al., "Distribution of liposomes into brain and rat brain tumor models by convection-enhanced delivery monitored with magnetic resonance imaging," Cancer Res, 64:2572-2579 (2004).
Sanhaji et al., "Polo-like kinase 1 inhibitors, mitotic stress and the tumor suppressor p53," Cell Cycle, 12:1340-1351 (2013).
Schöffski et al., "Multicentric parallel phase II trial of the polo-like kinase 1 inhibitor BI 2536 in patients with advanced head and neck cancer, breast cancer, ovarian cancer, soft tissue sarcoma and melanoma. The first protocol of the European Organization for Research and Treatment of Cancer (EORTC) Network of Core Institutes (NOCI)," Euro J Cancer, 46:2206-2215 (2010).
Sebastian et al., "The efficacy and safety of BI 2536, a novel Plk-1 inhibitor, in patients with stage 111B/IV non-small cell lung cancer who had relapsed after, or failed, chemotherapy: results from an open-label, randomized phase II clinical trial," J Thorac Oncol, 5:1060-1067 (2010).
Shin, S.W. et al., "Hepatic Intra-Arterial Injection of 3-bromopyruvate in Rabbit VX2 Tumor," Acta Radiologica, 47(10):1036-1041 (2006).
Singh et al., "Reduced Toxicity and Enhanced Antitumor Efficacy of Betacyclodextrin Plumbagin Inclusion Complex in Mice Bearing Ehrich Ascits Carcinoma," Indian J Physiol Pharmacol, 41(2): 171-175 (1997).
Soulen et al., "Intraarterial Chemotherapy with Limb-sparing Resection of Large Soft-tissue Sarcomas of the Extremities," JVIR, 3:659-663 (1992).
Sporn et al., "Chemoprevention of Cancer," Carcinogenesis, 21(3): 525-530 (2000).
Sprinson et al., "A study of β-hydroxy-α-keto acids," J Biol Chem, 164: 417-32 (1946).
Steegmaier et al., "BI 2536, a potent and selective inhibitor of polo-like kinase 1, inhibits tumor growth in vivo," Curr Biol, 17:316-322 (2007).
Stella et al., "Cyclodextrins," Toxicol Pathol, 36:30-42 (2008).
Stewart et al., "The polo-like kinase inhibitor BI 2536 exhibits potent activity against malignant plasma cells and represents a novel therapy in multiple myeloma," Exp Hematol, 39:330-338 (2011).
Supplementary European Search Report dated Aug. 30, 2011 from EP 09 80 8532.
Supplementary European Search Report for EP 07 86 9361 dated Jul. 26, 2011.
Sur et al., "A panel of isogenic human cancer cells suggests a therapeutic approach for cancers with inactivated p53," Proc Natl Acad Sci U S A, 106:3964-3969 (2009).
Sur et al., "Remote Loading of Preencapsulated Drugs into Stealth Liposomes," P Natl Acad Sci, 111(6): 2283-2288 (2014).
Szejtli, "Introduction and general overview of cyclodextrin chemistry," Chem Rev, 98:1743-1754 (1998).
Tang et al., "Facile synthesis of mono-6-amino-6-deoxy-alpha-, beta-, gamma-cyclodextrin hydrochlorides for molecular recognition, chiral separation and drug delivery," Nat Protoc, 3:691-697 (2008).
Thompson, "Cyclodextrins—enabling excipients: their present and future use in pharmaceuticals," Crit Rev Ther Drug, 14:1-104 (1997).
Torchilin, "Recent advances with liposomes as pharmaceutical carriers," Nat Rev Drug Discov, 4:145-160 (2005).
Uekama et al., "Cyclodextrin drug carrier systems," Chemical Rev, 98:2045-2076 (1998).
USPC Entry on Idarubicin hydrochloride (Jan. 4, 2002).

(56) References Cited

OTHER PUBLICATIONS

Vali et al., "Effects of Intraarterial Delivery of 3-Bromopyruvate on Tumor Apoptosis: Comparison of 1 Hr Infusion to Serial Bolus Injections in an Animal Model of Liver Cancer," Radiological Society of North America (RSNA), Scientific Assembly and Annual Meeting, (2005).
Vali et al., "Intraarterial Therapy with a New Potent Inhibitor of Tumor Metabolism (3-bromopyruvate): Identification of Therapeutic Dose and Method of Injection in an Animal Model of Liver Cancer," Journal of Vascular and Interventinal Radiology, 18(1):95-101 (2007).
Vali et al., "Targeting of VX2 Rabbit Liver Tumor by Selective Delivery of 3-Bromopyruvate: A Biodistribution and Survival Study", J Pharmacol Exp Ther, 327(1):32-37.
Vose et al., "The Plk1 inhibitor BI 2536 in patients with refractory or relapsed non-Hodgkin lymphoma: a phase I, open-label, single dose-escalation study," Leukemia & Lymphoma, 54:708-713 (2013).
Vossen et al., "Development of a new orthotopic animal model of metastatic liver cancer in the rabbit VX2 model: effect on metastases after partial hepatectomy, intra-arterial treatment with 3-bromopyruvate and chemoembolization," Clin Exp Metastasis 25(7):811-817 (2008).
Vyas et al., "Cyclodextrin based novel drug delivery systems," J Incl Phenom Macrocycl Chem, 62: 23-42 (2008).
Wang et al., "Isolated Lower Extremity Chemotherapeutic Infusion for Treatment of Osteosarcoma: Experimental Study and Preliminary Clinical Report," J. Vasc. Interv. Radiol., 12:731-737 (2001).
Wang et al., "Nanoparticle delivery of cancer drugs," Annu Rev Med, 63:185-198 (2012).
Warmus et al., "2-Alkylamino- and alkoxy-substituted 2-amino-1,3,4-oxadiazoles-O-Alkyl benzohydroxamate esters replacements retain the desired inhibition and selectivity against MEK (MAP ERK kinase)," Bioorg Med Chem Lett, 18:6171-6174 (2008).
Xu et al., "Inhibition of Glycolysis in Cancer Cells: a Novel Strategy to Overcome Drug Resistance Associated with Mitochondrial Respiratory Defect and Hypoxia," Cancer Res, 65(2): 613-621 (2005).
Yamada, K. et al., "Factors Influencing [F-18] 2-Fluoro-2-Deoxy-D-Glucose (F-18 FDG) Uptake in Melanoma Cells: The Role of Proliferation Rate, Viability, Glucose Transporter Expression and Hexokinase Activity," The J. of Dermatology, 32:316-334 (2005).
Yates et al., "Activation of insulin-secreting cells by pyruvate and halogenated derivatives," Biochm. J., 265:283-287 (1990).
Yun et al., "Spectrophotometric determination of bromopyruvate by reaction with 2-nitro-5-thiobenzoic acid," Anal Biochem, 85(2): 437-441 (1978).
Zhang et al., "Cyclodextrin-based Supramolecular Systems for Drug Delivery: Recent Progress and Future Perspective," Adv Drug Deliv Rev, 65(9): 1-39 (2013).
Zhang, et al., "Aerosolized 3-Bromopyruvate inhibits lung tumorigenesis without causing liver toxicity," Cancer Prev Res, 5(5): 717-725 (2012).
Zhu et al., "Pluronic F127-modified liposome-containing tacrolimus-cyclodextrin inclusion complexes: improved solubility, cellular uptake and intestinal penetration," J Pharm Pharmacol, 65:1107-1117 (2013).
Zucker et al., "Liposome drugs' loading efficiency: a working model based on loading conditions and drug's physicochemical properties," J Control Release, 139:73-80 (2009).

\* cited by examiner

FIG. 14

Oral 3-Bromopyruvate Treatment of Pancreatic Cancer

| DOSE | TUMOR SIZE TREATMENT START | DAYS OF TREATMENT | TUMOR SIZE TREATMENT END | MITOTIC INDEX |
|---|---|---|---|---|
| Control | 4-5mm$^3$ | 50 | 13-15mm$^3$ local spread | 10/field |
| 50mg/kg | 4-5mm$^3$ | 50 | 12-14mm$^3$ no spread | 9-10/field |
| 100mg/kg | 4-5mm$^3$ | 50 | 7-8mm$^3$ no spread | 7/field |
| 150mg/kg | 4-5mm$^3$ | 50 | 4-6mm$^3$ no spread | 2-4/field |
| 200mg/kg | 4-5mm$^3$ | 50 | 3-5mm$^3$ no spread | 1-2/field |

All doses given orally once daily in a volume of 250μl at a pH of 4-5.

FIG. 15

| Group | Total amount 3-BrPA (mg) | Total administered volume (ml) | Concentration (mg/ml) | Concentration (mmol/l) | pH |
|---|---|---|---|---|---|
| 1 | 5 | 50 | 0.10 | 0.60 | 4 |
| 2 | 5 | 100 | 0.05 | 0.30 | 4 |
| 3 | 5 | 150 | 0.03 | 0.20 | 4 |
| 4 | 5 | 200 | 0.03 | 0.15 | 4 |
| 5 | 5 | 300 | 0.02 | 0.10 | 4 |

METHODS AND COMPOSITIONS FOR ADMINISTRATION OF 3-HALOPYRUVATE AND RELATED COMPOUNDS FOR THE TREATMENT OF CANCER

RELATED APPLICATIONSH

This application claims the benefit of priority under 35 U.S.C. § 119(e) to Provisional Application Ser. No. 61/165,239, filed Mar. 31, 2009, Provisional Application Ser. No. 61/097,408, filed Sep. 16, 2008 and Provisional Application Ser. No. 61/090,793, filed Aug. 21, 2008, the contents of which are all incorporated by reference in their entirety.

BACKGROUND OF THE INVENTION

The knowledge that cancer cells rely on increased glycolysis rather than oxidative phosphorylation for survival is known as "The Warburg Hypothesis" (Warburg, O., Science, 123:309-314 (1956)). This concept constitutes the basis for using glycolysis and its associated enzymes as unique targets for the development of new anticancer therapeutic agents (Shaw, R. J., Curr. Opin. Cell Biol., 18:598-608 (2006); Gatenby, R. A. and Gillies, R. J., J. Biochem. Cell Biol., 39:1358-1366 (2007)). One such agent is 3-bromopyruvate (3-BrPA), a synthetic brominated derivative of pyruvic acid that acts as an irreversible glycolytic inhibitor (Ko et al., Cancer Lett., 173:83-91 (2001); Geschwind et al., Cancer Res., 62:3909-3913 (2002)). Early studies demonstrated that 3-BrPA is able to completely eradicate tumors implanted in rabbit livers when administered directly into the liver by intra-arterial injection, resulting in a significant survival benefit in advanced stages of the disease. The therapeutic dose was found to be to be 1.75 mM in 25 ml of phosphate-buffered saline (PBS), when given as a continuous, 1 hour intra-arterial infusion (Vali et al., J. Vasc. Interv. Radiol., 18:95-101 (2007)). Furthermore, when the animals were treated at a relatively early stage of their cancer, effective local control of the tumor resulted in the achievement of complete remission of the cancer. In addition to its excellent therapeutic profile, intra-arterially delivered 3-BrPA also had a favorable biodistribution profile with a high tumor uptake and no negative effects on healthy tissue (Vali et al., The Journal of Pharmacology and Experimental Therapeutics, 327(1):32-7 (2008)).

These results highlight that 3-BrPA is a highly promising anti-cancer agent. However, a major limitation for future clinical use of this compound is the fact that the preclinical testing was conducted using a rather uncommon delivery method for anti-cancer agents, i.e. intra-arterially directly into the liver. Because 3-BrPA is a non-specific alkylating agent, it is thought to be a highly toxic compound and it was believed that the intra-arterial approach was required to prevent systemic toxicities (Chang et al., Acad. Radiol., 14(1)85-92 (2007)).

Because intra-arterial administration is a technically challenging method for delivery an anti-cancer agent and is not applicable for every type of cancer, other 3-BrPA delivery methods are greatly desired.

SUMMARY

The present invention relates to novel methods and compositions for the administration of 3-halopyruvate and related anti-cancer compounds. The invention is based at least in part on the observation that safe administration of an effective concentration of 3-halopyruvate or 3-halopyruvate related compounds could be achieved if the compound was administered in a formulation with a pH of between 2 and 6.

In some embodiments, the invention relates to a method of treating cancer in a subject that includes administering to the subject an effective amount of a pharmaceutical composition that contains a pharmaceutical agent represented by the general formula:

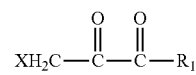

wherein, independently of each occurrence:

X represents a halide, a sulfonate, a carboxylate, an alkoxide, or an amine oxide;

$R_1$ represents OR, H, $N(R'')_2$, C1-C6 alkyl, C6-C12 aryl, C1-C6 heteroalkyl, or C6-C12 heteroaryl;

R" represents H, C1-C6 alkyl, or C6-C12 aryl;

R represents H, alkali metal, C1-C6 alkyl, C6-C12 aryl or C(O)R'; and

R' represents H, C1-C20 alkyl or C6-C12 aryl;

and wherein the pharmaceutical composition has an acidity of greater than or equal to about pH 2 and less than or equal to about pH 6. In some embodiments the acidity of the pharmaceutical composition is greater than or equal to about pH 3 and less than or equal to about pH 5. In certain embodiments the acidity of the pharmaceutical composition is pH 4.

In some embodiments of the invention, the pharmaceutical agent is 3-halopyruvate. In certain embodiments the pharmaceutical agent is 3-bromopyruvate.

In certain embodiments, the pharmaceutical composition is administered orally. In some embodiments the pharmaceutical agent is administered at a dose of greater than or equal to about 150 milligrams per kilogram of body weight and less than or equal to about 250 milligrams per kilogram of body weight.

In some embodiments of the invention, the pharmaceutical composition further includes $NaHCO_3$. In certain embodiments, the molar concentration of the pharmaceutical agent is within 5 fold or 2 fold of the molar concentration of $NaHCO_3$. In some embodiments the molar concentration of the pharmaceutical agent is about equal to the molar concentration of $NaHCO_3$. In some embodiments, the molar concentration of the pharmaceutical agent is less than about 2 M. In certain embodiments, the molar concentration of the pharmaceutical agent is about 1 M. In some embodiments the concentration of the pharmaceutical agent is less than or equal to about 0.03 milligrams per milliliter.

In some embodiments, the methods of the invention further include the administration of a chemotherapeutic agent. In some instances, chemotherapeutic agent is altretamine, asparaginase, BCG, bleomycin sulfate, busulfan, camptothecin, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin—dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, topotecan, vinblastine, vincristine or vinorelbine tartrate.

In some embodiments, the invention relates to a method of treating a solid tumor. In certain embodiments the invention relates to the treatment of liver cancer, pancreatic cancer, lung cancer, or breast cancer.

Certain aspects of the invention relate to the pharmaceutical composition that contains a pharmaceutical agent represented in the general formula:

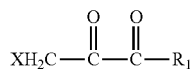

wherein, independently of each occurrence:

X represents a halide, a sulfonate, a carboxylate, an alkoxide, or an amine oxide;

$R_1$ represents OR, H, N(R")$_2$, C1-C6 alkyl, C6-C12 aryl, C1-C6 heteroalkyl, or C6-C12 heteroaryl;

R" represents H, C1-C6 alkyl, or C6-C12 aryl;

R represents H, alkali metal, C1-C6 alkyl, C6-C12 aryl or C(O)R';and

R' represents H, C1-C20 alkyl or C6-C12 aryl;

and wherein the pharmaceutical composition has an acidity of greater than or equal to about pH 2 and less than or equal to about pH 6. In some embodiments the acidity of the pharmaceutical composition is greater than or equal to about pH 3 and less than or equal to about pH 5. In certain embodiments the acidity of the pharmaceutical composition is pH 4.

In some embodiments of the invention, the pharmaceutical agent is 3-halopyruvate. In certain embodiments the pharmaceutical agent is 3-bromopyruvate.

In certain embodiments the pharmaceutical composition is formulated for oral administration.

In some embodiments of the invention, the pharmaceutical composition further includes NaHCO$_3$. In certain embodiments, the molar concentration of the pharmaceutical agent is within 5 fold or 2 fold of the molar concentration of NaHCO$_3$. In some embodiments the molar concentration of the pharmaceutical agent is about equal to the molar concentration of NaHCO$_3$.

In certain embodiments of the invention, the pharmaceutical composition further includes a chemotherapeutic agent. In some embodiments the chemotherapeutic agent is altretamine, asparaginase, BCG, bleomycin sulfate, busulfan, camptothecin, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin—dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, topotecan, vinblastine, vincristine or vinorelbine tartrate.

In some embodiments, the invention relates to kits containing the pharmaceutical compositions of the invention.

Panel B shows the ATP levels (cell viability) of Hep3B, HepG2, SK-Hep1 and VX2liver cancer cells when treated with various concentrations of 3-BrPA for 24 hours.

Panel C shows the ATP levels (cell viability) of Hep3B, HepG2, SK-Hep1 and VX2liver cancer cells when treated with various concentrations of 3-BrPA for 48 hours.

Figure 5:
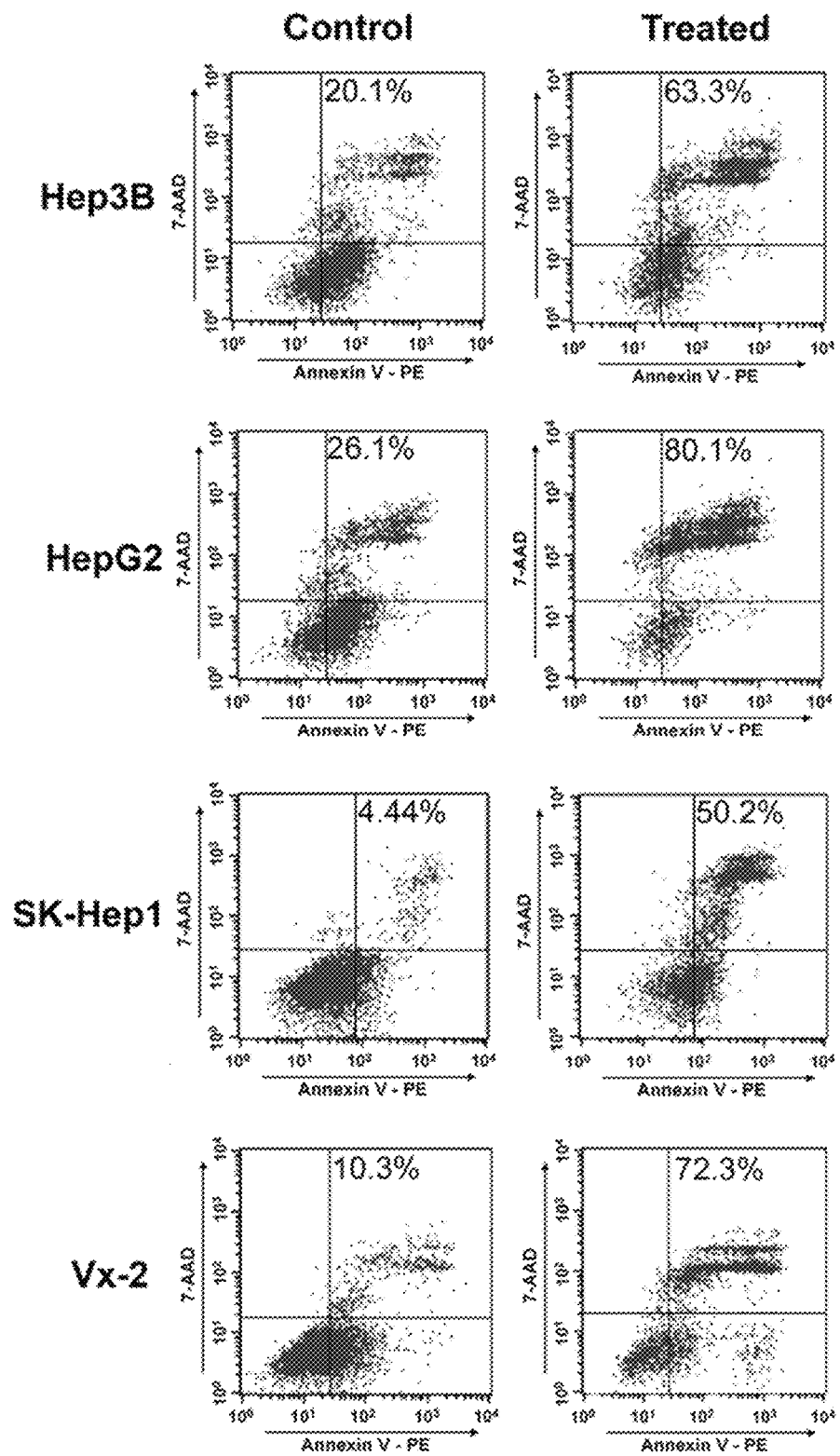

FIG. 5 shows the flow cytometry analysis of 7-AAD and Anexin V levels of Hep3B, HepG2, SK-Hep1 and VX2liver cancer cells when untreated (Control) or treated with 200μM 3-BrPA for 2 hours (Treated).

Figure 6:
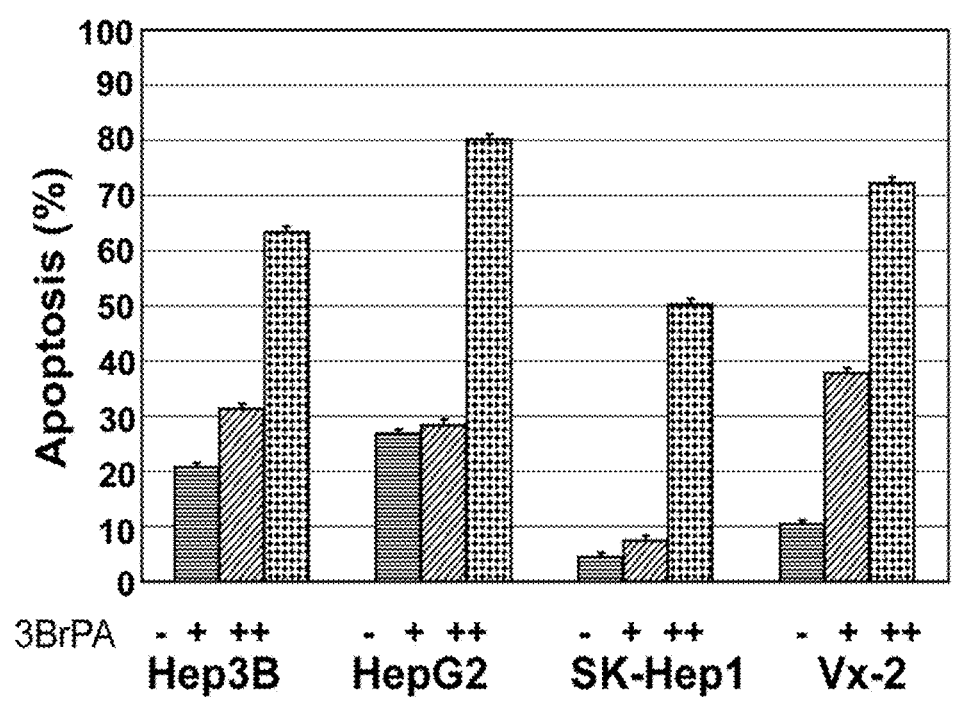

FIG. 6 shows the percent of Hep3B, HepG2, SK-Hep1 and VX2liver cancer cells undergoing apoptosis following treatment with 0 μM (−), 100 μM (+) or 200 μM (++) 3-BrPA.

Figure 7:
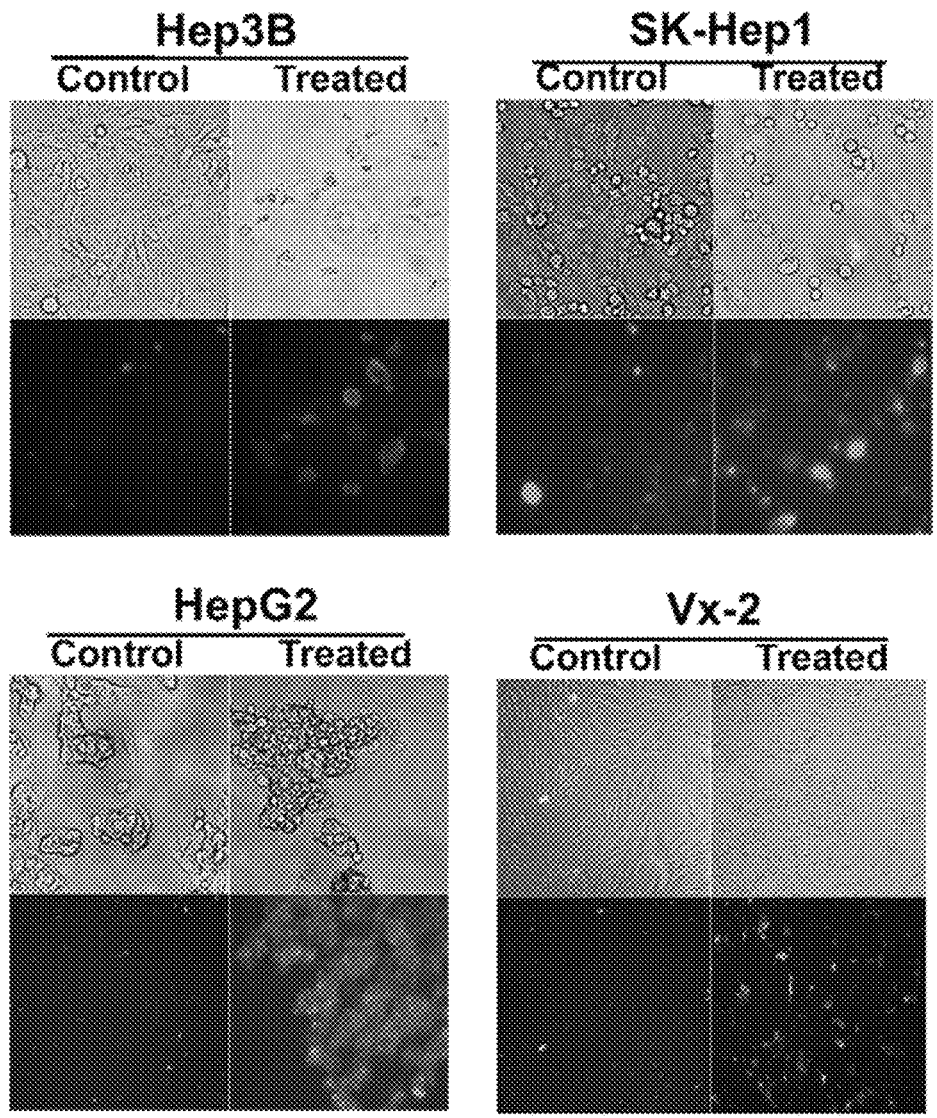

FIG. 7 shows fluorescent and light micrographs of Annexin V stained Hep3B, HepG2, SK-Hep1 and VX2liver cancer cells.

Figure 8:
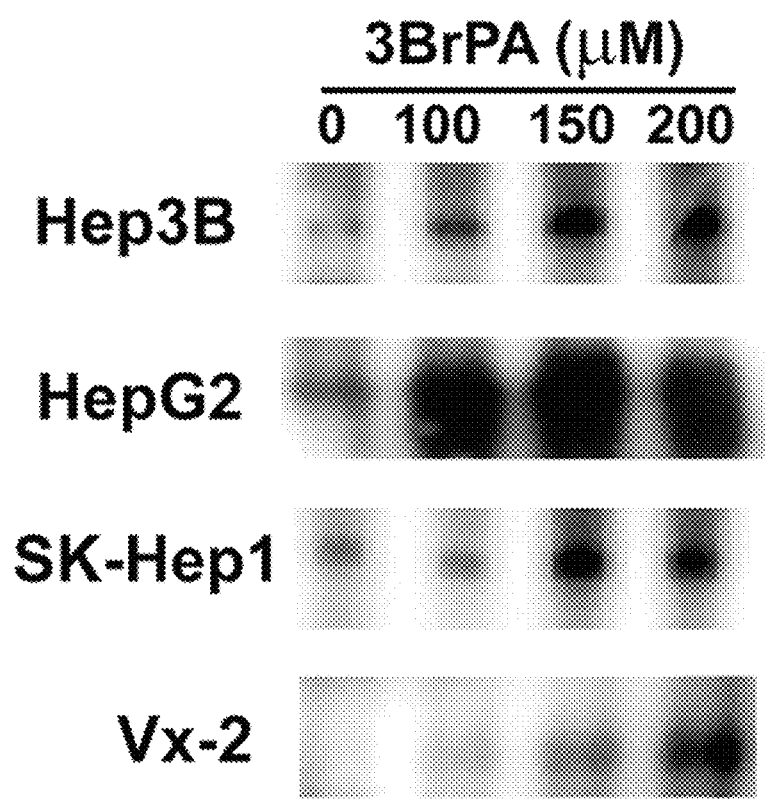

FIG. 8 shows a western blot of activated Caspase 3 using lysates from Hep3B, HepG2, SK-Hep1 and VX2liver cancer cells treated with 0 μM, 100 μM, 150 μM or 200 μM 3-BrPA.

Figure 9:
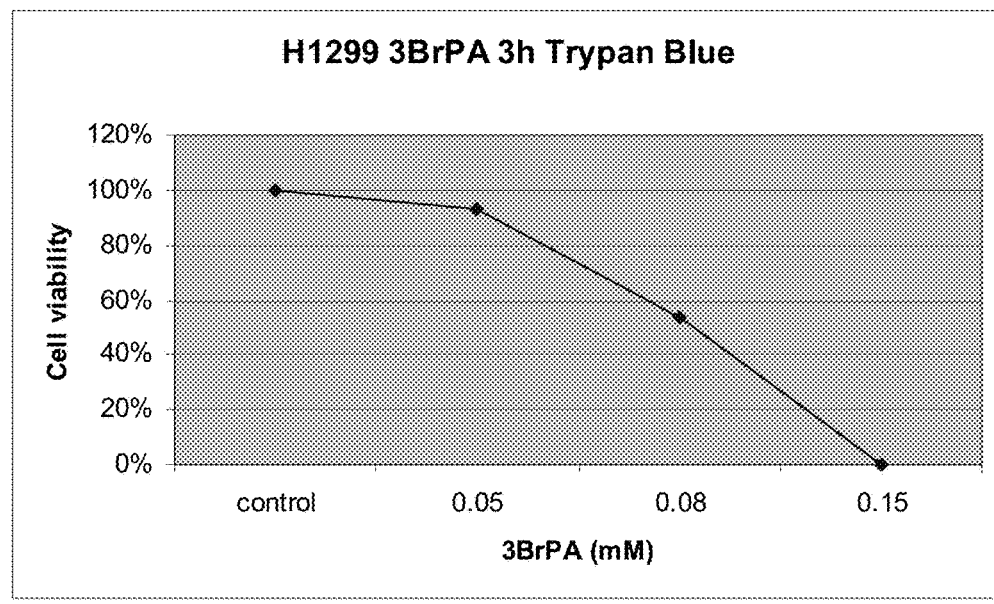

FIG. 9 shows the cell viability of H1299lung cancer cells when treated untreated (control) or treated with various concentrations of 3-BrPA.

Figure 10:
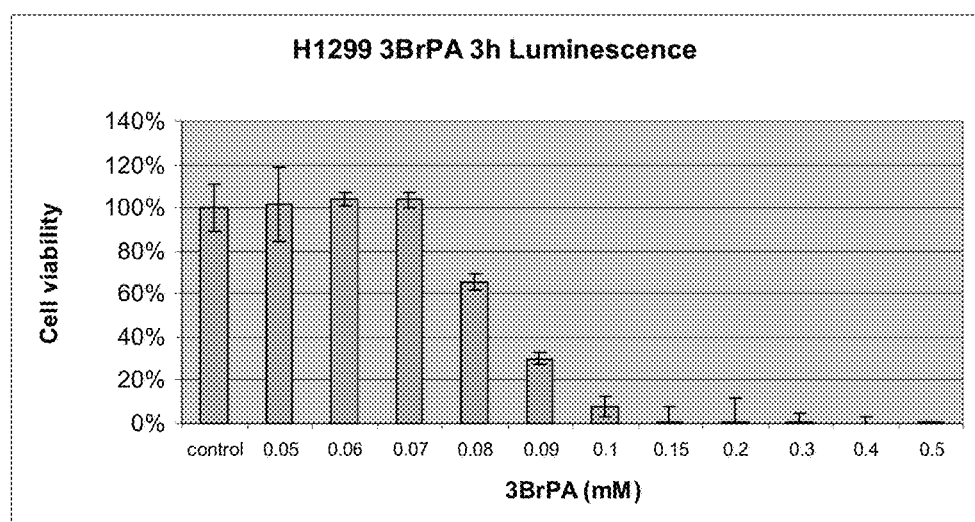

FIG. 10 shows the ATP levels (cell viability) of H1299lung cancer cells when treated untreated (control) or treated with various concentrations of 3-BrPA.

Figure 11:
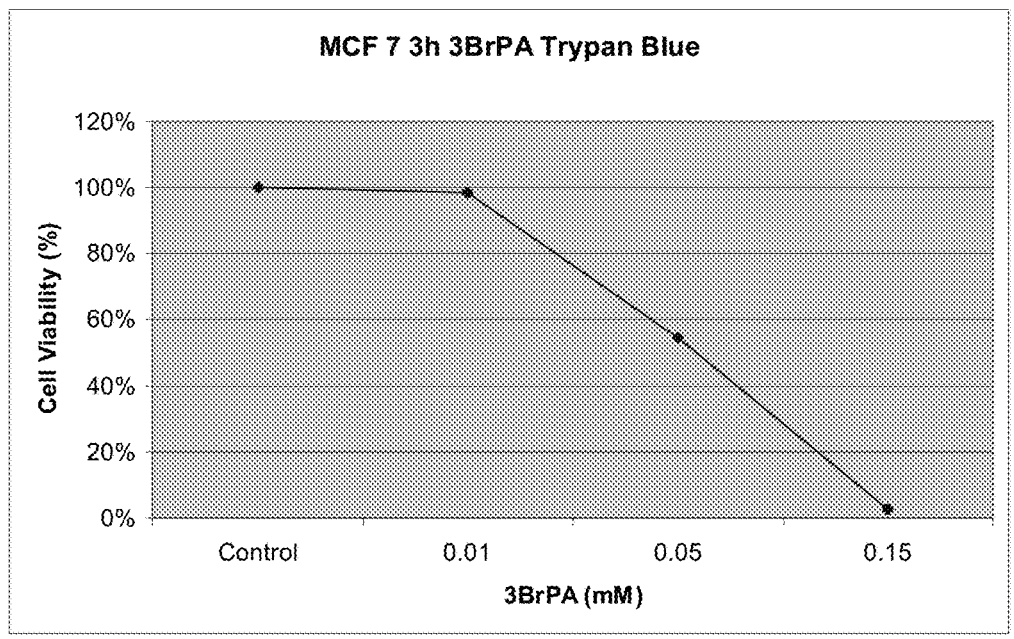

FIG. 11 shows the viability of MCF7breast cancer cells when treated untreated (control) or treated with various concentrations of 3-BrPA.

Figure 12:
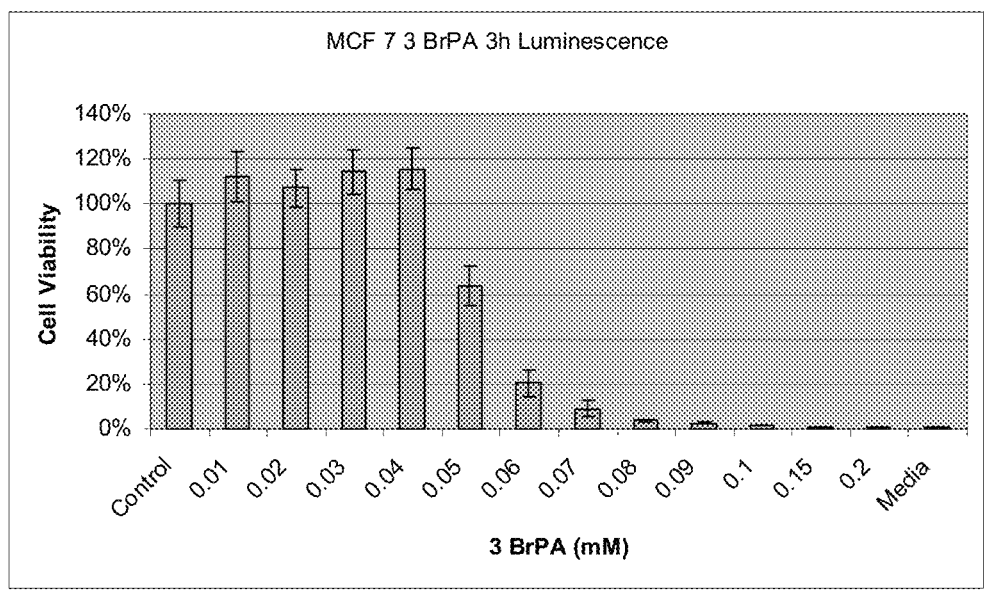

FIG. 12 shows the ATP levels (cell viability) of MCF7breast cancer cells when treated untreated (control) or treated with various concentrations of 3-BrPA.

Figure 13:
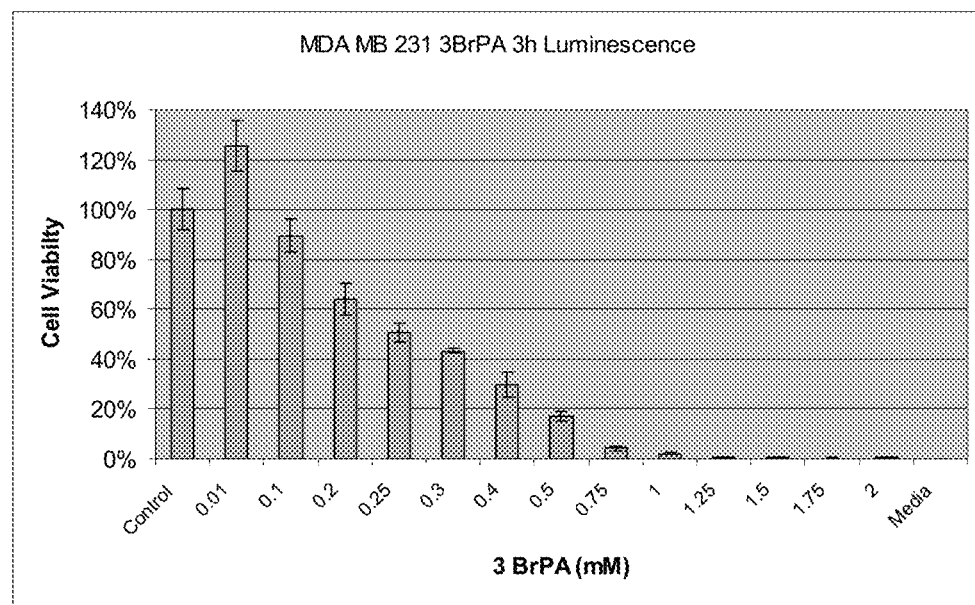

FIG. 13 shows the ATP levels (cell viability) of MDA MB 231 breast cancer cells when treated untreated (control) or treated with various concentrations of 3-BrPA.

FIG. 14 shows the tumor size and mitotic index in pancreatic tumors taken from orthotopic xenograft pancreatic cancer model mice after 50 days of 3-BrPA treatment.

FIG. 15 shows total amount, volume and concentration of 3-BrPA administered to nude mice to determine the effect of 3-BrPA concentration on the tolerability of oral 3-BrPA administration.

DETAILED DESCRIPTION

1. Definitions

The present invention provides novel methods and compositions for the administration of 3-halopyruvate as an anti-cancer agent. In order for the present invention to be more readily understood, certain terms and phrases are defined below and throughout the specification.

"Therapeutic agent" or "pharmaceutical agent" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, non-specific (e.g. non-antibody) proteins, oligonucleotides (e.g., antisense oligonucleotides that bind to a target nucleic acid sequence (e.g., mRNA sequence)), peptides, and peptidomimetics.

The articles "a" and "an" are used herein to refer to one or to more than one (i.e., to at least one) of the grammatical object of the article. By way of example, "an element" means one element or more than one element.

"Therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

"Modulation" refers to up regulation (i.e., activation or stimulation), down regulation (i.e., inhibition or suppression) of a response, or the two in combination or apart.

The phrases "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

As used herein, the term "subject" means a human or non-human animal selected for treatment or therapy.

As used herein, the term "subject suspected of having" means a subject exhibiting one or more clinical indicators of a disease or condition. In certain embodiments, the disease or condition is cancer. In certain embodiments, the cancer is leukemia or lymphoma.

As used herein, the term "subject in need thereof" means a subject identified as in need of a therapy or treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic salts of compounds.

The term "3-bromopyruvate" or "3-BrPA" as used herein refers to 3-bromopyruvate, analogs and derivatives of 3-bromopyruvate, prodrugs of 3-bromopyruvate, metabolites of 3-bromopyruvate and salts thereof.

As used herein, the term "cancer" includes, but is not limited to, solid tumors and blood borne tumors. The term cancer includes diseases of the skin, tissues, organs, bone, cartilage, blood and vessels. The term "cancer" further encompasses primary and metastatic cancers.

As used herein, the term "administering" means providing a pharmaceutical agent or composition to a subject, and includes, but is not limited to, administering by a medical professional and self-administering.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

2. Selective Inhibitors of ATP Production

Some embodiments of the invention relate to the use of 3-halopyruvate and related compounds in the treatment of cancer. In some embodiments the 3-halopyruvate is 3-bromopyruvate.

In one aspect, the invention provides selective inhibitors of ATP production represented by the general formula:

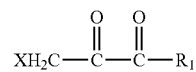

wherein X represents a halide, a sulfonate, a carboxylate, an alkoxide, or an amine oxide. In certain embodiments, X is a halide selected from the group consisting of: fluoride, bromide, chloride, and iodide. In one embodiment, the inhibitor is a 3-halopyruvate. In certain other embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate and may be selected from the group consisting of: triflate, mesylate and tosylate. In yet another embodiment, X is an amine oxide is dimethylamine oxide. In certain embodiments $R_1$ represents OR, H, N(R")$_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R represents H, alkali metal, C1-C6 alkyl, C6-C12 aryl or C(O)R'; and R' represents H, C1-C20 alkyl or C6-C12 aryl.

In a preferred embodiment, the invention further provides inhibitors of ATP production represented by general formula:

wherein X represents a halide, a sulfonate, a carboxylate, an alkoxide, or an amine oxide. In certain embodiments, X is a halide and may be selected from the group consisting of: fluoride, bromide, chloride, and iodide. In one embodiment, the inhibitor is 3-halopyruvate. In certain embodiments, the 3-halopyruvate is selected from the group consisting of: 3-fluoropyruvate, 3-chloropyruvate, 3-bromopyruvate and 3-iodopyruvate. In one embodiment, the 3-halopyruvate is 3-bromopyruvate. In other embodiments, X is a sulfonate selected from the group consisting of: triflate, mesylate and tosylate. In yet another embodiment, X is an amine oxide is dimethylamine oxide.

Other analogs, derivatives, prodrugs, metabolites and salts thereof of 3-bromopyruvate may also be used, provided that these compounds or compositions have an anticancerous effect that is statistically similar to that of 3-bromopyruvate. When referring herein to a treatment using 3-bromopyruvate, it should be understood that the treatment may also be conducted with analogs, derivatives, prodrugs, metabolites and salts of 3-bromopyruvate, where applicable.

3. Pharmaceutical Compositions of the Subject Inhibitors

The invention provides pharmaceutical compositions comprising 3-bromopyruvate as well as other inhibitor compounds described above. In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect the compounds of the invention can be administered as such or in admixtures with pharmaceutically acceptable carriers and can also be administered in conjunction with other chemotherapeutic agents and/or scavenger compounds. Conjunctive therapy thus includes sequential, simultaneous and separate, or co-administration of the active compound, wherein the therapeutic effects of the first administered has not entirely disappeared when the subsequent compound is administered.

In some embodiments the pharmaceutical composition of the invention is formulated so as to have a specific pH. In some embodiments the pH of the pharmaceutical composition of the invention is greater than or equal to about pH 0.5, 1.0, 1.5, 2.0, 2.5, 3.0, 3.1, 3.2, 3.3, 3.4, 3.5, 3.6, 3.7, 3.8, 3.9 or 4.0. In some embodiments the pH of the pharmaceutical composition of the invention is less than or equal to about pH 9.0, 8.0, 7.0, 6.5, 6.0, 5.5, 5.0, 4.9, 4.8, 4.7, 4.6, 4.5, 4.4, 4.3, 4.2, 4.1 or 4.0. The pH of the pharmaceutical composition can be determined by any method known in the art or calculated based on the chemical properties of the molecules that make up the pharmaceutical composition. The pH of a pharmaceutical composition of the invention can be adjusted to a desired level using any technique known in the art. In some embodiments a buffer is used to establish and/or maintain a desired pH in a pharmaceutical composition of the invention. In some embodiments, a desired pH of the pharmaceutical composition is established by using Sodium Bicarbonate (NaHCO$_3$). In some embodiments the molar concentration of NaHCO$_3$ in the pharmaceutical composition is greater than or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 6.0, 7.0, 8.0, 9.0, 10.0, 15, 20, 25, 50 or 100 times the molar concentration of 3-BrPA in the pharmaceutical composition. In some embodiments the molar concentration of 3-BrPA in the pharmaceutical composition is greater than or equal to 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 6.0, 7.0, 8.0, 9.0, 10.0, 15, 20, 25, 50 or 100 times the molar concentration of NaHCO$_3$ in the pharmaceutical composition.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the present compounds may contain a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Exemplary formulations comprising 3-bromopyruvate are determined based on various properties including, but not limited to, chemical stability at body temperature, functional efficiency time of release, toxicity and optimal dose.

The preparations of the present invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compounds according to the invention may be formulated for administration in any convenient way for use in human or veterinary medicine, by analogy with other pharmaceuticals.

In certain embodiments, the above-described pharmaceutical compositions comprise one or more of the inhibitors, a second chemotherapeutic agent, and optionally a pharmaceutically acceptable carrier.

The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following drugs may also be used in combination with an antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons $\alpha$, $\beta$, and $\gamma$; hormones, such as luteinizing hormone releasing hormone (LHRH) and analogues and, gonadotropin releasing hormone (GnRH); growth factors, such as transforming growth factor-$\beta$ (TGF-$\beta$), fibroblast growth factor (FGF), nerve growth factor (NGF), growth hormone releasing factor (GHRF), epidermal growth factor (EGF), fibroblast growth factor homologous factor (FG-FHF), hepatocyte growth factor (HGF), and insulin growth factor (IGF); tumor necrosis factor-$\alpha$ & $\beta$ (TNF-$\alpha$ & $\beta$); invasion inhibiting factor-2 (IIF-2); bone morphogenetic proteins 1-7 (BMP 1-7); somatostatin; thymosin-$\alpha$-1; $\gamma$-globulin; superoxide dismutase (SOD); complement factors; anti-angiogenesis factors; antigenic materials; and pro-drugs.

Chemotherapeutic agents for use with the compositions and methods of treatment described herein include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In another embodiment, the composition of the invention may comprise other biologically active substances, including therapeutic drugs or pro-drugs, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically active.

4. Therapeutic Methods

The present invention further provides novel therapeutic methods of treating cancer, including a cancerous tumor comprising administering to a subject, (e.g., a subject in need thereof), an effective amount of 3-bromopyruvate or related compound. A subject in need thereof may include, for example, a subject who has been diagnosed with a tumor, including a pre-cancerous tumor, a cancer, or a subject who has been treated, including subjects that have been refractory to the previous treatment.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The pharmaceutical compositions of the present invention may be delivered by any suitable route of administration, including orally, nasally, as by, for example, a spray, rectally, intravaginally, parenterally, intracisternally and topically, as by powders, ointments or drops, including buccally and sublingually. In certain embodiments the pharmaceutical compositions are delivered generally (e.g., via oral or parenteral administration). In certain other embodiments the pharmaceutical compositions are delivered locally through direct injection into a tumor or direct injection into the tumor's blood supply (e.g., arterial or venous blood supply). In some embodiments, the pharmaceutical compositions are delivered by both a general and a local administration. For example, a subject with a tumor may be treated through direct injection of a composition containing 3-BrPA into the tumor or the tumor's blood supply in combination with oral administration of a pharmaceutical composition of the present invention. If both local and general administration is used, local administration can occur before, concurrently with and/or after general administration.

In certain embodiments, the methods of treatment of the present invention, including treating a cancerous or precancerous tumor comprise administering 3-bromopyruvate in conjunction with a second agent to the subject. Such methods in certain embodiments comprise administering pharmaceutical compositions comprising 3-bromopyruvate or a related compound in conjunction with one or more chemotherapeutic agents and/or scavenger compounds, including chemotherapeutic agents described herein, as well as other agents known in the art. Conjunctive therapy includes sequential, simultaneous and separate, or co-administration of the active compound in a way that the therapeutic effects of the first compound administered one have not entirely disappeared when the subsequent compound is administered. In one embodiment, the second agent is a chemotherapeutic agent. In another embodiment, the second agent is a scavenger compound. In another embodiment, the second agent is radiation therapy. In a further embodiment, radiation therapy may be administered in addition to 3-bromopyruvate and a second agent. In certain embodiments, the second agent may be co-formulated in the separate pharmaceutical composition.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the composition per kg body weight of the patient. For example, a range of amounts of compositions are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the compounds of the invention will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In certain embodiments, the compounds of the invention will be administered in a pharmaceutical composition. In some embodiments the molar concentration of the compound of the invention in the pharmaceutical composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the compound of the invention will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Alternatively, the dosage of the subject invention may be determined by reference to the plasma concentrations of the composition. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use 3-bromopyruvate and related compounds and a second agent, e.g. another chemotherapeutic agent or a scavenger compound, may reduce the required dosage for any individual compound and/or agent because the onset and duration of effect of the different compounds and/or agents may be complimentary.

As described above, 3-bromopyruvate or related compounds may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 minutes, wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods to administer radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant. In contrast, radiopharmaceuticals are unsealed sources of radiation that may be given orally, intravenously or directly into a body cavity.

Radiation therapy may also include sterotactic surgery or sterotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

EXEMPLIFICATION

The invention now being generally described will be more readily understood by reference to the following examples which are included merely for purposes of illustration of certain aspects and embodiments of the present invention, and are not intended to limit the invention in any way.

Materials and Methods

Animal Model

New Zealand White rabbits were used in the study. All rabbits, carriers and recipients, were anesthetized with a mixture of acepromazine (2.5 mg/kg; Phoenix, St. Joseph, Mo.) and ketamine hydrochloride (44 mg/kg; Phoenix) administered intramuscularly. The VX2 tumor cell suspension was first injected into the hind legs of carrier rabbits and grown for 2 weeks. Resultant tumors were harvested from each carrier and a tumor suspension was prepared from each harvested tumor by dissection of viable tumor tissue and aseptic mincing.

For the rabbits that were going to receive the VX2 tumor implanted in the liver, intravenous access was gained via a marginal ear vein and 0.1-0.2 ml (2.5-5 mg) of sodium pentobarbital (Abbott Laboratories, Abbott Park, Ill.) was given periodically to maintain anesthesia. The abdomen of each recipient rabbit was shaved and disinfected with ethanol and povidine iodine. The liver of the rabbit was exposed by a midline incision, then an aliquot of the tumor cell suspension (0.2 ml) was injected directly using a 21-gauge angiocatheter into the left lobe of the liver in order to develop a solitary lesion with adequate surrounding liver parenchyma. The abdomen was closed in two layers. The tumor was allowed to grow in the rabbit livers for 7 days. Pain and distress levels were assessed by daily by monitoring food intake, feces and urine production and finally checking for signs of guarding or reluctance to move when touched. Animals were euthanized 6 months after initiation of the treatment or when they became moribund or showed signs of distress (e.g. irregular behavior, lethargy, or >20% weight loss).

Cells and Reagents

The non-small cell lung cancer (NSCLC) cell line NCI-H1299, the breast cancer cell lines MCF7 and MDA MB 231 and the Hep3B, Hep2G and SK-Hep1 cells were obtained from the American Type Culture Collection (ATCC) (Manassas, Va., USA) and maintained as a monolayer culture in Eagle's minimum essential medium (MEM, Invitrogen, Gaithersburg, Md., USA) supplemented with 10% fetal bovine serum at 37 C and 5% $CO_2$. All treatments were done in triplicate samples on 96-well plates. VX2 cells were maintained as described in Geschwind et al., Cancer Res., 62:3909-3913 (2002).

ATP Dependant Luminescence Cell Viability Assay

Cytotoxicity of 3-BrPA was evaluated by the $IC_{50}$ values, representing the drug concentration which depletes ATP by 50% compared to non-treated control. On day 1, cells were seeded into 96-well plates in a volume of 100 µl per well. On day 2, the medium of all wells was removed and an aliquot of 100 µl of media having serial dilutions of 3-BrPA in PBS, $NaHCO_3$, NaOH, KOH and $KHCO_3$ was added to the appropriate well. After 24 h of drug exposure cytotoxic effects of 3-BrPA were monitored by cellular ATP level using CellTiter-Glo™ assay reagents from Promega Corp (Madison, Wis.). Briefly, 100 µl assay reagent was added to each well and mixed at room temperature for 2 min to develop luminescent signal. The luminescence intensity (cps) from each sample was determined with a spectrometer (Model Victor III, Perkin Elmer, Mass.). Relative luminescence was calculated in proportion to the numbers of living cells per sample well. The results are expressed as the mean of three independent experiments. The intracellular ATP contents were calculated and normalized by equal cell number and expressed as the percentage of the control cells. The $IC_{50}$ values were estimated graphically from dose-response plots.

Apoptosis Assays

The apoptosis of 3-BrPA treated cells was evaluated using Annexin V staining and the formation of active caspase-3. Cells treated with 3-BrPA were stained with anti-Annexin V and analyzed by flow cytometry as well as fluorescent microscopy. Flow cytometry was performed using a Becton-Dickinson FACSCalibur. The gating was done based on unstained control cells, Annexin V—PE stained and 7-AAD stained control cells. For fluorescent microscopy, Annexin V staining was performed using Annexin V staining Microscopy kit (BD Biosciences, USA) according to the protocol recommended by the manufacturer. In brief, cells grown in chambered slides were treated with either 3BrPA or the vehicle, washed once with ice-cold PBS followed by two washes with binding buffer, at the end of the treatment period. Cells were then incubated with the FITC-conjugated Annexin V fluorescent antibody for 15 min followed by a gentle wash. The cells were kept in binding buffer and images were observed captured using a Zeiss Axiovert 200 Microscope (Carl Zeiss Microimaging Inc., USA). Active caspase-3, an apoptotic marker, was identified by western blot analysis. Lysates prepared from equal numbers of cells treated with different concentrations of 3BrPA were subjected to SDS-PAGE electrophoresis and immunoblotting against active (cleaved) caspase-3.

Example 1

Oral Administration of 3-BrPA Dissolved in PBS

Preclinical studies of 3-BrPA as a cancer agent have utilized direct intra-arterial injection into the liver as the drug delivery method. Though intra-arterial injection reduces the risk of systematic toxicity, it is a technically challenging delivery method that is not applicable to all forms of cancer. Formulations of 3-BrPA for oral administration were therefore examined.

Figure 1:
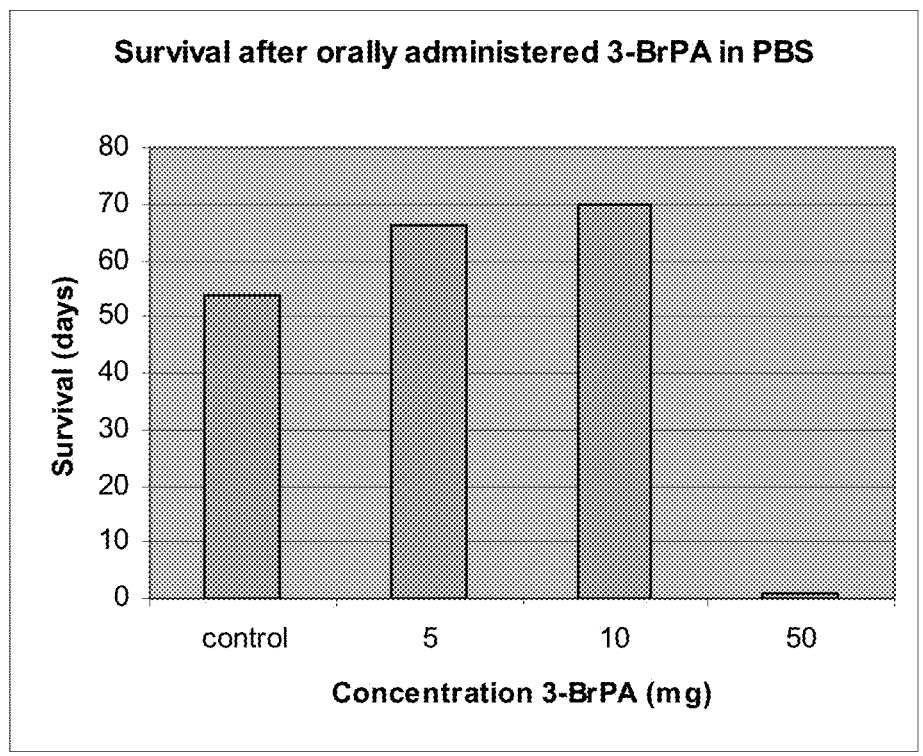
FIG. 1 shows the survival time of VX2tumor bearing rabbits that had received no treatment (control),5 mg of 3-BrPA in PBS, 10 mg of 3-BrPA in PBS, or 50 mg of 3-BrPA in PBS.

Oral administration of 3-BrPA dissolved in PBS was examined using the VX2 tumor model, an animal model for hepatocellular carcinoma (described above). VX2 tumors were allowed to grow the livers of 12 New Zealand White rabbits for 10 days. Tumor bearing rabbits were divided in 4 groups. Group 1 (n=3) received 5 mg of 3-BrPA in 2.75 ml of Phosphate Buffered Saline (PBS) orally once a day, group 2 (n=3) received 10 mg of 3-BrPA in 2.75 ml of PBS orally once a day, group 3 (n=3) received 50 mg of 3-BrPA in 2.75 ml of PBS orally once a day and group 4 (control, n=3) received no treatment. Results of the experiment are shown in FIG. 1. Median survival for the animals in group 1 (n=3), receiving 5 mg of 3-BrPA in 2.75 ml of PBS, was 66 days. Animals in group 2 (n=3), receiving 10 mg of 3-BrPA in 2.75 ml of PBS, survived for 70 days. All the animals in group 3 (n=3), receiving 50 mg of 3-BrPA in 2.75 ml of PBS expired within 24 hours of oral administration of the first dose. Control animals showed a median survival of 54 days.

Example 2

Oral Administration of 3-BrPA Dissolved in $NaHCO_3$

Based on the results described in Example 1, it was concluded that 10 mg of 3-BrPA is the maximum tolerated dose (MTD) if dissolved in 2.75 ml of PBS. In order to enable administration of 3-BrPA in a higher dose, and thus improve survival, the efficacy of 3-BrPA when dissolved in several alternative buffers was tested in vitro. When dissolved in $NaHCO_3$, 3-BrPA did not show a significantly different in $IC_{50}$ value as determined by an ATP luminescent assay (described above) when compared to 3-BrPA dissolved in PBS. On the other hand, other buffers tested (NaOH, KOH and $KHCO_3$), resulted in significantly higher $IC_{50}$ values.

Figure 2:
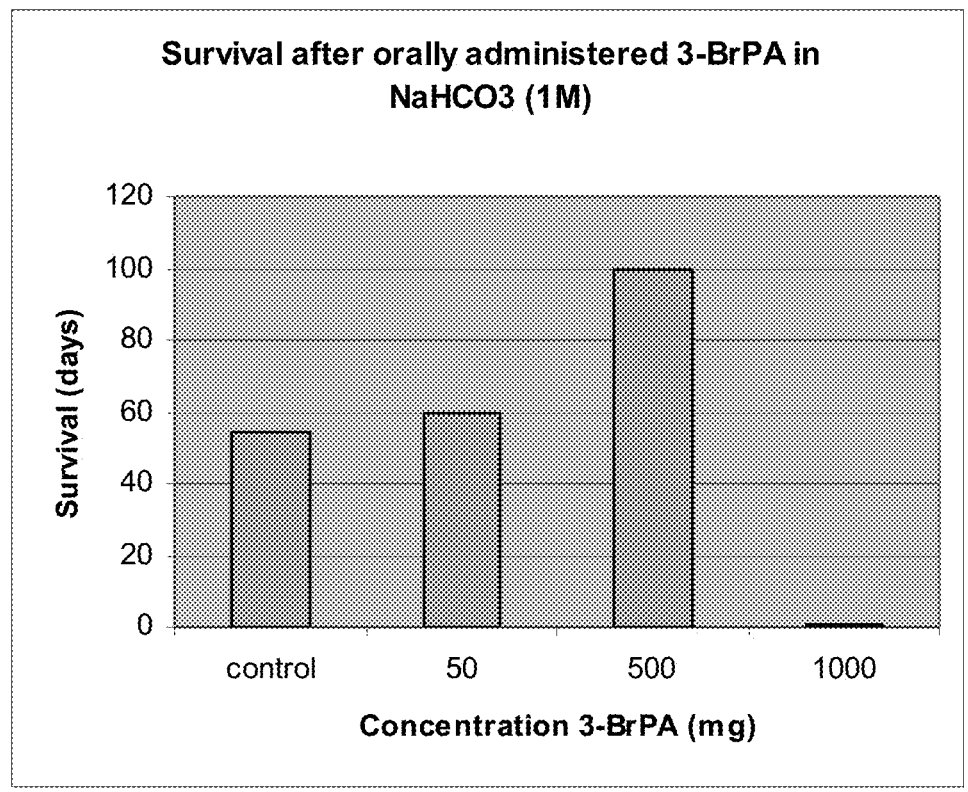
FIG. 2 shows the survival time of VX2tumor bearing rabbits that had received no treatment (control), 50 mg of 3-BrPA in 1M NaHCO$_3$, 500 mg of 3-BrPA in 1M NaHCO$_3$, or 1000 mg of 3-BrPA in 1M NaHCO$_3$.

To test whether buffering 3-BrPA with $NaHCO_3$ would allow oral administration of a higher dose of 3-BrPA, the maximum tolerated dose of orally administered 3-BrPA dissolved in $NaHCO_3$ was determined. As in Example 1, the VX2 tumor model was used, with VX2 tumors grown in the livers of 12 New Zealand White rabbits for 10 days. Once again, the tumor bearing rabbits were divided in 4 groups. As shown in FIG. 2, median survival for the animals in group 1 (n=3) receiving 50 mg of 3-BrPA in 2.75 ml of $NaHCO_3$ (1M) orally once a day was 60 days. The animals in group 2 (n=3) received 500 mg of 3-BrPA in 2.75 ml of $NaHCO_3$ orally once a day survived and had a median survival time of 100 days. All animals in group 3 (n=3) expired within 24 hours after receiving 1000 mg of 3-BrPA in 2.75 ml of NaHCO$_3$ orally. Control animals that did not receive 3-BrPA had a median survival of 54 days.

Based on these results it was concluded that 500 mg of 3-BrPA is the MTD if buffered with 2.75 ml of 1M NaHCO$_3$. This dose is a 50 fold increase compared to the MTD of 3-BrPA in PBS. Significantly, the rabbits that received the MTD of 3-BrPA buffered with 2.75 ml of NaHCO$_3$ survived 42% longer than rabbits treated with the MTD of 3-BrPA buffered with PBS and 79% longer than rabbits that did not receive the 3-BrPA treatment.

The animals treated with the MTD of 3-BrPA buffered with NaHCO$_3$ died of aspiration, whereas the other rabbits died due to the tumor itself. Mean liver tumor size in the animals treated with the MTD of 3-BrPA buffered with NaHCO$_3$ was <0.5 cm, whereas mean liver tumor size in all other groups was >8 cm. The rabbits treated with the MTD of 3-BrPA buffered with NaHCO$_3$ showed no metastases, whereas all other rabbits showed widespread metastases on pathology.

The effect of pH on the survival of rabbits bearing VX2 liver tumors that were treated with the MTD of 3-BrPA buffered with NaHCO3 was examined. The VX2 tumor model was once again used, as described above. A total of 20 New Zealand White rabbits were included in the study. All rabbits received VX2 tumor implantation as described above. The tumor was allowed to grow in the rabbit livers for 7 days. Rabbits were divided in 4 groups. Group 1 (n=6) received 500 mg of 3-BrPA in 2.75 ml of NaHCO3 (1 M, resulting in pH 4), group 2 (n=2) received 500 mg of 3-BrPA in 2.75 ml of PBS (resulting in pH<2), group 3 (n=6) received 500 mg of 3-BrPA in 2.75 ml of NaHCO3 (2 M, resulting in pH 7) and group 4 (n=6) received no treatment (control group). All drugs were administered orally once a day.

Figure 3:
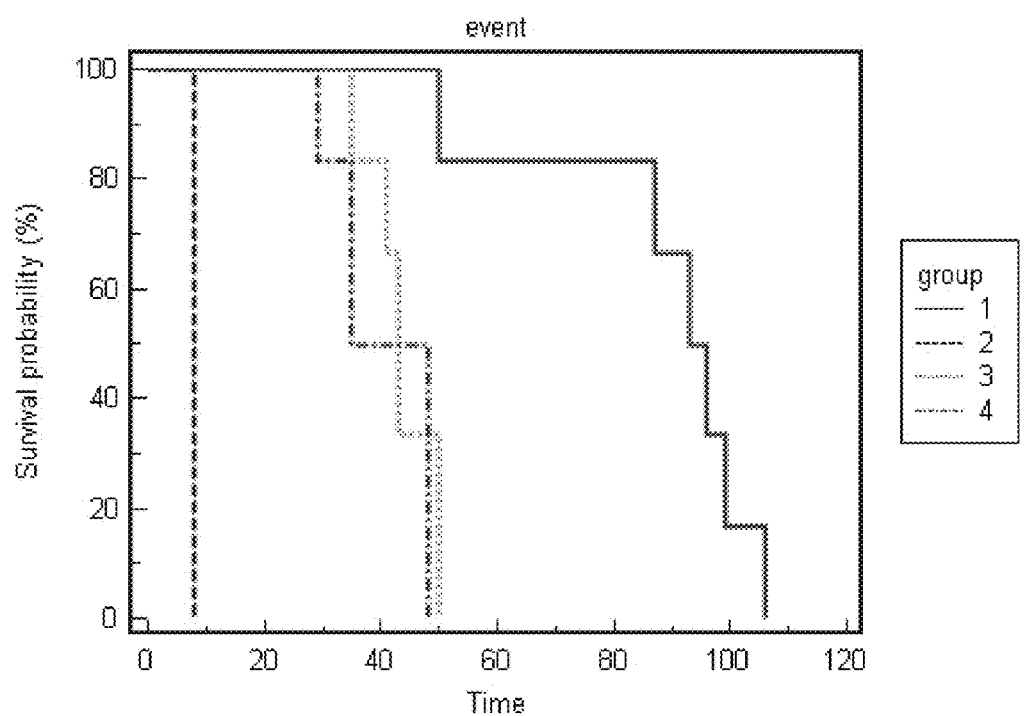
FIG. 3 shows the survival time of VX2tumor bearing rabbits that had received 500 mg of 3-BrPA in a pH 4Sodium Bicarbonate buffered solution (Group 1), 500 mg of 3-BrPA in PBS (Group 2), 500 mg of 30BrPA in a pH 7 Sodium Bicarbonate buffered solution (Group 3), or no treatment (Group 4).

As shown in FIG. 3, Kaplan Meier analysis of animal survival showed a significant survival benefit for rabbits treated with 500 mg of 3-BrPA in 2.75 ml of NaHCO3 (1 M, resulting in pH 4) (Group 1) compared to rabbits in group 2 (500 mg of 3-BrPA in 2.75 ml of NaHCO3 (0.1 M resulting in pH<2.0)), group 3 (500 mg of 3-BrPA in 2.75 ml of NaHCO3 (2 M, resulting in pH 7)) and group 4 (control group, untreated with 3-BrPA). These data underscored the importance and sensitivity of the buffering conditions used in administration of therapeutic doses of 3-BrPA. Unbuffered 3-BrPA, with a pH<2, resulted in immediate death, while buffering conditions that resulted in a pH>6 rendered 3-BrPA less effective as a cancer therapeutic.

Example 3

The Effect of 3-BrPA on Liver Cancer Cells

The efficacy of 3-BrPA in the treatment of liver cancer cells was further tested using the cancer cell lines Hep3B, HepG2, SK-Hep1 and VX2. As described above, the cell lines were grown as monolayers in MEM (Invitrogen) supplemented with 10% fetal bovine serum (HyClone) at 37 C.° and 5% CO$_2$, and all treatments were done in triplicate samples on 96-well plates.

Figure 4A:
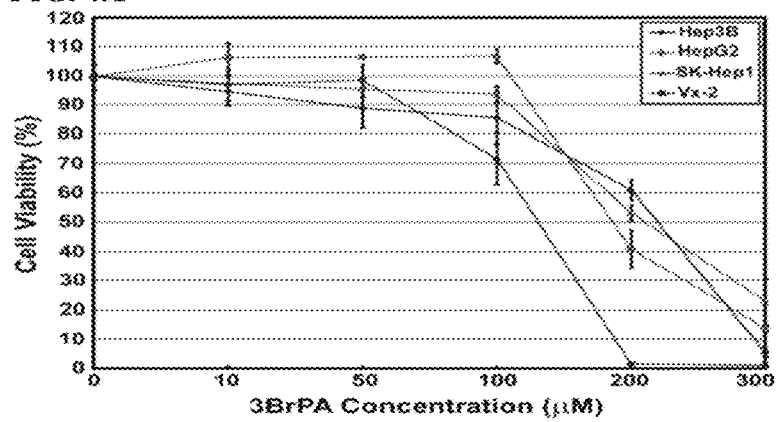
FIG. 4 includes three panels, identified as panels A, B, C. Panel A shows the ATP levels (cell viability) of Hep 3B, HepG 2, SK-Hep1 and VX2liver cancer cells when treated with various concentrations of 3-BrPA for 3hours.
Figure 4B:
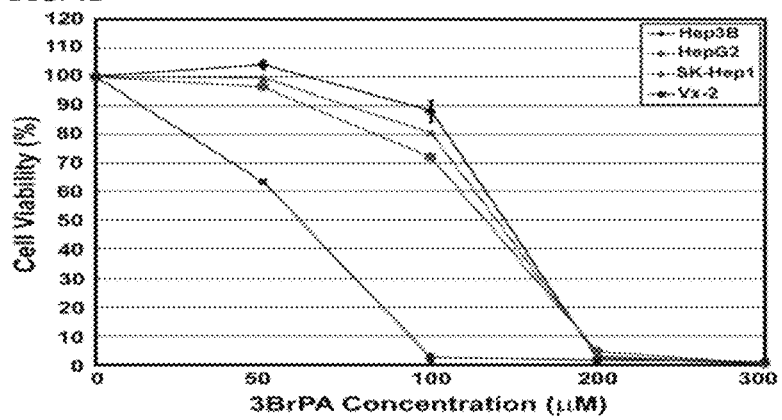
Figure 4C:
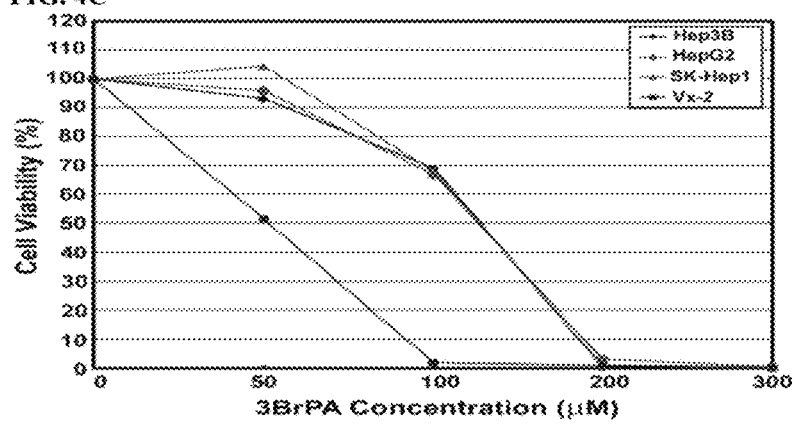

The effects on cell viability and cellular metabolism of 3-BrPA on Hep3B and VX2 cells were examined using luminescence ATP assays, as described above. The level of ATP is an indicator of metabolic activity as well as energy status of living cells, which decreases as the cells undergo apoptosis or necrosis. Treatment with 3-BrPA resulted in a dose and time dependent decrease in the level of ATP in all four cell lines (FIG. 4A-4C). The IC$_{50}$ value at of 3-BrPA was 130 to 145 μM for HepG2, Hep3B and SK-Hep 1 cells and 60 μM for the Vx-2 cell line, and 125 μM for HepG2, Hep3B and SK-Hep 1 cells and 50 μM for the Vx-2 cell line at 48 hours. Thus, increasing the duration of 3BrPA treatment results in decreased IC$_{50}$ values for the cell lines. These results further substantiate the anti-glycolytic and energy depleting properties of 3-BrPA in liver cancer cells.

Flow cytometric analysis of Annexin V-PE and 7-AAD stained Hep3B, HepG2, SK-Hep1 and VX2 cells that were treated with 3-BrPA showed a dose dependent increase in Annexin V positive cells, indicating an elevated levels of apoptosis in 3-BrPA treated cells (FIGS. 5 and 6). Compared with control, a significant increase the number of apoptotic cells was observed in all cell lines tested after 2 hours of treatment with 3-BrPA (FIG. 5).

In order to confirm that the cytotoxic effects of 3BrPA involves cellular apoptotic pathways, Annexin V levels and Caspase-3 activation was examined in cells treated with 3-BrPA. FIG. 7 shows photomicrographs of Annexin V stained cells either with (Treated) or without (Control) 3-BrPA treatment. The elevated levels of Annexin V in the 3-BrPA treated cells indicate that 2-BrPA induces cell death through apoptosis. Additionally, immunoblotting of cell lysates with activated-Caspase-3 specific antibodies confirmed the activation of caspase-3 during 3BrPA mediated cell death (FIG. 8). A dose dependent increase in Caspase-3 activation was evident in all four of the cell lines treated with 3BrPA. Overall, these results support the inference that the 3BrPA promotes apoptosis in 3-BrPA treated liver cancer cells and confirms that orally administered 3-BrPA may be an effective treatment of liver cancer.

Example 4

The Effect of 3-BrPA on Lung Cancer Cells

The efficacy of 3-BrPA in the treatment of lung cancer cells was tested using the non-small cell lung cancer (NSCLC) cell line NCI-H1299. As described above, the cell line was grown as a monolayer in MEM (Invitrogen) supplemented with 10% fetal bovine serum (HyClone) at 37 C.° and 5% CO$_2$, and all treatments were done in triplicate samples on 96-well plates.

Trypan blue viability assays revealed a dose and time dependent decrease in viability, after 3-BrPA treatment, in H1299 cells (FIG. 9). At a concentration of 0.1 mM, more than 80% of the cells died within 3 hours, and 100% cell death was achieved at 0.2 mM. The EC$_{50}$ of 3-BrPA for H1299 cells lies between 0.08 and 0.09 mM. Notably, the EC$_{50}$ value for 3-BrPA for H1299 lung cancer cells was lower than the EC$_{50}$ of 3-BrPA for VX2 liver cancer cells, indicating that the lung cancer cell line is more sensitive to 3-BrPA than the liver cancer cell line. Therefore, considering that oral administration of 3-BrPA buffered in NaHCO$_3$ is effective in prolonging survival in liver cancer models (Example 2), it is probable that oral administration of 3-BrPA buffered in NaHCO$_3$ would also be effective in the treatment of lung cancer.

The anti-metabolic effect of 3-BrPA on H1299 cells was examined using luminescence ATP assays, as described above. The level of ATP is an indicator of metabolic activity as well as energy status of living cells, which decreases as the cells undergo apoptosis or necrosis. Bioluminescent quantification of ATP in 3-BrPA treated H1299 cells showed a dose and time dependent energy (ATP) depletion (cell viability, FIG. 10). This further substantiates the anti-glycolytic and energy depleting properties of 3-BrPA in lung cancer cells, and suggests that orally administered 3-BrPA may be an effective treatment of lung cancer.

Example 5

The Effect of 3-BrPA on Breast Cancer Cells

The efficacy of 3-BrPA in the treatment of breast cancer cells was tested using the cancer cell lines MCF7 and MDA MB 231. As described above, the cell lines were grown as monolayers in MEM (Invitrogen) supplemented with 10% fetal bovine serum (HyClone) at 37 C.° and 5% $CO_2$, and all treatments were done in triplicate samples on 96-well plates.

Trypan blue viability assays revealed a dose and time dependent decrease in viability, after 3-BrPA treatment, in MCF7 cells (FIG. 11). At a concentration of 0.05 mM, more than 40% of the cells died within 3 hours and 100% cell death was achieved at 0.15 mM. The $EC_{50}$ of 3-BrPA for MCF7 cells lies between 0.05 and 0.06 mM. The $EC_{50}$ value for 3-BrPA for MCF7 breast cancer cells was lower than the $EC_{50}$ of 3-BrPA for VX2 liver cancer cells, indicating that the breast cancer cell line is more sensitive to 3-BrPA than the liver cancer cell line. Therefore, considering that oral administration of 3-BrPA buffered in $NaHCO_3$ is effective in prolonging survival in liver cancer models (Example 2), it is probable that oral administration of 3-BrPA buffered in $NaHCO_3$ would also be effective in the treatment of breast cancer.

The anti-metabolic effect of 3-BrPA on MCF7 and MDA MB231 cells was examined using luminescence ATP assays, as described above. The level of ATP is an indicator of metabolic activity as well as energy status of living cells, which decreases as the cells undergo apoptosis or necrosis. Bioluminescent quantification of ATP in 3-BrPA treated MCF7 cells (FIG. 12) and MDA MB 231 cells (FIG. 13) showed a dose and time dependent energy (ATP) depletion (cell viability). This further substantiates the anti-glycolytic and energy depleting properties of 3-BrPA in breast cancer cells, and suggests that orally administered 3-BrPA may be an effective treatment of breast cancer.

Example 6

The Effect of 3-BrPA on Pancreatic Cancer

The efficacy of orally administered 3-BrPA in the treatment of pancreatic cancer was tested using an orthotopic xenograft pancreatic cancer model. Human PANC-10 pancreatic cancer cells were implanted into the pancreas of NOD/SCID mice and allowed to form 4-5 $mm^3$ sized tumors. Following the establishment of the tumors, tumor-bearing mice were orally administered 250 µl of a $NaHCO_3$-buffered solution containing varying concentrations of 3-BrPA once per day. After 50 days of treatment, the tumor-bearing mice were sacrificed and tumor growth and cancer cell proliferation was analyzed.

Administration of 3-BrPA reduced the growth of pancreatic cancer in the tumor-bearing mice. At day 50, the tumors in mice that had not been administered 3-BrPA (control) had grown to a size of 13-15 $mm^3$, and there was evidence of local tumor metastases to other parts of the pancreas. The tumors of mice that had been administered $NaHCO_3$-buffered 3-BrPA at a daily dose of 50 mg/kg had grown to be 12-14 $mm^3$ in size, but lacked any signs of local metastases. The tumors of mice that had been administered $NaHCO_3$-buffered 3-BrPA at a daily dose of 100 mg/kg had grown to be 7-8 $mm^3$ in size, and also lacked any signs of local metastases. The tumors of mice that had been administered $NaHCO_3$-buffered 3-BrPA at a daily dose of 150 mg/kg had grown to be 4-6 $mm^3$ in size, and lacked any signs of local metastases. The tumors of mice that had been administered $NaHCO_3$-buffered 3-BrPA at a daily dose of 200 mg/kg showed no signs of growth (tumors were 3-5 $mm^3$ in size at day 50), and lacked any signs of local metastases. The results of these experiments are summarized in FIG. 14.

The mitotic index of the pancreatic tumors of the 3-BrPA treated mice was analyzed using microscopy in order to determine the how different doses of 3-BrPA affected the proliferation of the pancreatic cancer cells. The tumors in mice that had not been administered 3-BrPA (control) had a mitotic index of 10 mitotic cells per field. The tumors of mice that had been administered $NaHCO_3$-buffered 3-BrPA at a daily dose of 50 mg/kg had a mitotic index of 9-10 mitotic cells per field. The tumors of mice that had been administered $NaHCO_3$-buffered 3-BrPA at a daily dose of 100 mg/kg had a mitotic index of 7 mitotic cells per field. The tumors of mice that had been administered $NaHCO_3$-buffered 3-BrPA at a daily dose of 150 mg/kg had a mitotic index of 2-4 mitotic cells per field. The tumors of mice that had been administered $NaHCO_3$-buffered 3-BrPA at a daily dose of 200 mg/kg had a mitotic index of 1-2 mitotic cells per field. The results of these experiments are also summarized in FIG. 14.

Example 7

The Effect of 3-BrPA Concentration on the Maximum Tolerable Dose

As demonstrated herein, buffering with $NaHCO_3$ allows oral administration of a higher doses of 3-BrPA. To determine the effect of compound concentration on the tolerable dose of 3-BrPA, a series of experiments were performed in nude mice to determine how a change in administered volume, and therefore a change 3-BrPA concentration, would influence compound efficacy and animal survival. For these experiments, 3-BrPa was administered at a dose of 200 mg/kg and a pH of 4. FIG. 15 shows the values of the administered doses.

All mice in group 1 and 2 (n=3 per group) died within 24 hours after receiving 5 mg of 3-BrPA in volumes of 50, and 100 ml, respectively. Mice in groups 3, 4 and 5, receiving 3-BrPA in volumes of 150, 200 and 300 ml respectively, did not show any signs of discomfort, and survived daily 3-BrPA administration without any apparent ill-effects.

General toxicology studies were conducted on nude mice that were orally administered $NaHCO_3$-buffered 3-BrPA at doses of 0, 100 and 200 mg/kg/day. The duration of exposure in this study ranged from a single dose to 3-months of daily dosing. There were no mortalities in this study and animals did not exhibit any treatment related clinical symptoms. 3-BrPA treatment had no effect on body weight. Organ weights, gross pathology and histopathology did not show any treatment-related changes in any of the organs examined.

Example 8

3-BrPA does not Bind to Genomic DNA

Many antineoplastic chemotherapeutics are alkylating agents that exert their effect by binding to DNA and interfering with cell replication. This results in cumulative toxicities that are dose limiting. Since 3-BrPA has been reported to be an alkylating agent, it was determined whether 3-BrPA is incorporated into the DNA of 3-BrPA treated cells. To accomplish this, genomic DNA was isolated from SK-Hep and Hep3B cells that had been exposed to $^{14}$C-3-BrPA. Scintillation counting of the isolated genomic DNA demonstrated no evidence of $^{14}$C incorporation, indicating that 3-BrPA does not bind to genomic DNA.

EQUIVALENTS

The present invention provides, among other things, therapeutic compositions and methods of treating cancer using 3-bromopyruvate, related compounds, and other selective inhibitors of ATP production. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entirety as if each individual publication or patent was specifically and individually indicated to be incorporated by reference. In case of conflict, the present application, including any definitions herein, will control.

We claim:

1. A pharmaceutical composition formulated for oral administration comprising 3-bromopyruvate wherein the pharmaceutical composition has pH 3 to pH 5, and where the pharmaceutical composition further comprises NaHCO$_3$.

2. The pharmaceutical composition of claim 1, wherein a molar concentration of the pharmaceutical agent is within 5 fold of a molar concentration of NaHCO$_3$.

3. The pharmaceutical composition of claim 1, wherein a molar concentration of the pharmaceutical agent is within 2 fold of a molar concentration of NaHCO$_3$.

4. The pharmaceutical composition of claim 1, wherein a molar concentration of the pharmaceutical agent is about equal to a molar concentration of NaHCO$_3$.

5. The pharmaceutical composition of claim 1, wherein the pharmaceutical composition has an acidity of pH 4.

6. The pharmaceutical composition of claim 1, further comprising a chemotherapeutic agent.

7. The pharmaceutical composition of claim 6, wherein the chemotherapeutic agent is selected from a group consisting of: altretamine, asparaginase, BCG, bleomycin sulfate, busulfan, camptothecin, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, topotecan, vinblastine, vincristine and vinorelbine tartrate.

8. A kit comprising the pharmaceutical composition of claim 1.

9. The pharmaceutical composition of claim 1 for use in a method of treating liver cancer by orally administering the composition cancer.

* * * * *